United States Patent [19]

Albright et al.

[11] Patent Number: 5,459,131

[45] Date of Patent: Oct. 17, 1995

[54] RENIN INHIBITORS

[75] Inventors: Jay D. Albright, Nanuet, N.Y.; Charles F. Howell, Upper Saddle River, N.J.

[73] Assignee: American Cyanamid Company, Wayne, N.J.

[21] Appl. No.: 669,717

[22] Filed: Mar. 15, 1991

[51] Int. Cl.[6] .................... A61K 38/00; C07K 5/00; C07K 7/00; C07K 17/00
[52] U.S. Cl. .................. 514/19; 514/18; 530/330; 546/278; 548/200
[58] Field of Search ............... 514/18, 19; 530/330; 546/278; 548/200

OTHER PUBLICATIONS

Plattner et al., "Renin Inhibitors, Dipeptide Analogues," J. Med. Chem. 1988, 31, 2277–2288.
Burger, "Medicinal Chemistry," second edition, pp. 565–571, 578–581, 600–601 (1960).
Denkewalter et al., "Progress in Drug Research," vol. 10, pp. 510–512 (1966).
Bolis et al., "Renin Inhibitors, Dipeptide Analogues," J Med Chem. 1987, 30, 1729–1737.
Haber et al., "Renin Inhibitors" A Search for Principles of Design. J. Card. Pharm., 10 (Suppl. 7):S54–S58 (1987).

*Primary Examiner*—Jill Warden
*Assistant Examiner*—Sheela J. Huff
*Attorney, Agent, or Firm*—Richard K. Jackson

[57] ABSTRACT

Renin inhibiting compounds of the formula:

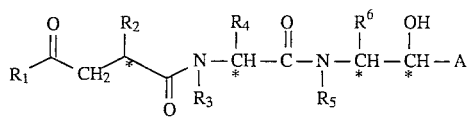

wherein A is a moiety selected from those of the formula:

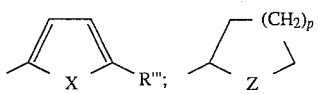

where Z is O, S, SO, or $SO_2$, P is 1 or 2 and X is —O— or —S—;

and analogs thereof which inhibit the substrate-cleaving acting of renin, pharmaceutical compositions containing these compounds, processes for producing the compounds and methods of treating hypertension which employ the novel renin inhibitors.

24 Claims, No Drawings

RENIN INHIBITORS

FIELD OF THE INVENTION

This invention relates to new compounds containing a single α-amino acid which inhibit renin and are thus useful in treating hypertension.

BACKGROUND OF THE INVENTION

Renin is an endopeptidase which plays an important role in the control of blood pressure. The renin angiotensin in system is a multiregulated proteolytic cascade in which renin cleaves the protein substrate angiotensinogen to give the relatively inactive decapeptide angiotensin I. Angiotensin converting enzyme (ACE) catalyses the removal of the terminal dipeptide from angiotensin I to form the highly active octapeptide angiotensin II which exhibits potent pressor activity. In addition to its direct vasoconstricting effect, angiotensin II also stimulates the adrenal cortex to release aldosterone, which leads to sodium retention and a rise in extracellular fluid volume. Thus, the renin-angiotensin system plays a key role in the regulation of blood pressure and is implicated in some forms of hypertension.

In an effort to develop agents useful in the treatment of hypertension, compounds called ACE inhibitors have been developed which inhibit angiotensin I converting enzyme thereby blocking the generation of angiotensin II and its vasopressive effect; these include captopril and enalapril maleate. Similarly, effective inhibitors of renin have been sought which would reduce the release of angiotensin I and ultimately lead to a reduction in the circulating level of angiotensin II. Thus, renin inhibitors would be useful alternatives to ACE inhibitors as therapeutic agents in the treatment of hypertension and congestive heart failure.

A number of prior art references have described peptide compounds that have activity as renin inhibitors. For example, Boger et al., Nature, 303, 81–84, (1983) describe peptide renin inhibitors containing the amino acid statine. See also Veber et al., U.S. Pat. Nos. 4,384,994 and 4,478,826. However, because these compounds are peptides, many of them are unsuitable for oral administration because of their proteolytic lability and poor absorption from the digestive tract. Smaller peptides that are better absorbed orally have proven to be poor inhibitors of renin. Recent efforts have been focused on formulating compounds which are effective orally yet retain high potency as inhibitors of human renin.

Recently, Iizuka and coworkers have described peptide renin inhibitors containing an unnatural amino acid, norstatine, (J. Med. Chem. Vol. 31, 701–704, 1988) which are active orally.

Other compounds having renin inhibiting activity have been disclosed which involve modifications to the N-terminal units, for example, Luly et al. U.S. Pat. Nos. 4,826,815, Sham, et al. 4,826,958, Iizuka et al. EP-0,206,807-A3, EP-0,190,891-A2, U.S. Pat. No. 4,656,269 and Hanson et al. Biochem. Biophys. Res. Comm., 160, 1–5 (1989). Certain modifications to the central amino acid structure have also been tried, see for example, Patchett et al. U.S. Pat. No. 4,839,357 and Bock et al. U.S. Pat. No. 4,663,310. Finally, modifications in the C-terminal substituents are disclosed in Boger et al. U.S. Pat. No. 4,782,043 and U.S. Pat. No. 4,885,292. The latter reference discloses compounds having heterocyclic nitrogen containing rings of 5 or 6 carbon atoms at the C-terminal unit.

The present invention relates to structurally novel renin inhibitors containing a single α-amino acid. The present compounds differ from the prior art in the novel C-terminal units and/or the central α-amino acid.

SUMMARY OF THE INVENTION

This invention relates to new dipeptide derivatives of general Formula I:

$$R_1-\overset{O}{\overset{\|}{C}}-CH_2-\overset{R_2}{\underset{*}{\overset{|}{C}H}}-\overset{O}{\overset{\|}{C}}-N-\overset{R_4}{\underset{*}{\overset{|}{C}H}}-\overset{O}{\overset{\|}{C}}-N-\overset{R_6}{\underset{*}{\overset{|}{C}H}}-\overset{OH}{\underset{*}{\overset{|}{C}H}}-A \quad \text{Formula I}$$
$$\phantom{xxxxxxxxxxxxxxxxxxxxxxx}R_3\phantom{xxxxxx}R_5$$

wherein $R_1$ is phenyl,

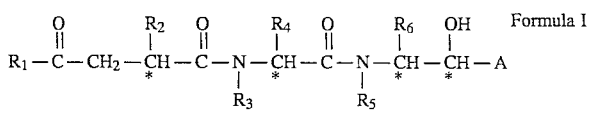

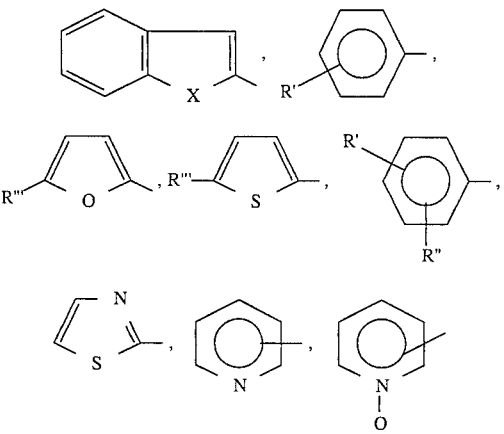

$R'$ is hydrogen, chloro, fluoro, methoxy, methyl, trifluoromethyl, $-SO_2NH_2$,

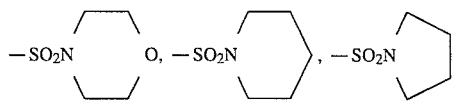

$-SO_2NH$ lower alkyl $(C_1-C_6)$; $-SO_2N$ (lower alkyl)$_2$; $R''$ is chloro, fluoro, methyl, methoxy, $R'''$ is hydrogen, chloro, fluoro, lower alkyl $(C_1-C_6)$;

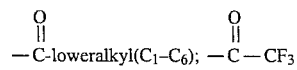

$R_2$ is phenylmethyl, cyclohexylmethyl, lower alkyl $(C_1-C_6)$,

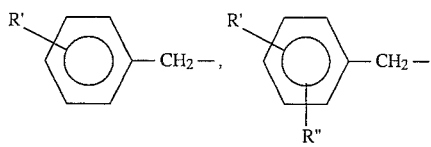

1-naphthalenylmethyl, (benzo[b]-thien-3-yl)methyl, (benzo[b]-thien-2-yl)methyl, (3-benzofuranyl)methyl, (2-benzofuranyl)methyl; $R_3$ is hydrogen or methyl; $R_4$ is alkyl $(C_1-C_8)$; phenylmethyl, cyclohexylmethyl; 4-imidazolylmethyl; (4-imidazolyl)$CH_2X$;

X-alkyl($C_1$-$C_9$); —($CH_2$)$_n$N[lower alkyl ($C_1$-$C_3$)]$_2$; —($CH_2$)$_n$—NH alkyl($C_1$-$C_3$); X-cyclohexyl, —($CH_2$)$_n$—X-alkyl($C_1$-$C_3$), —X—$CH_2CH_2$N[alkyl($C_1$-$C_3$)]$_2$ (where X is —O— or —S— and n is 1 to 4) and moieties of the formula:

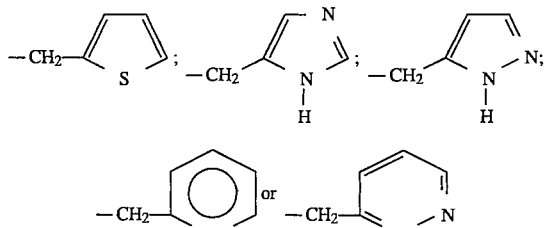

$R_5$ is hydrogen or methyl; $R_6$ is alkyl($C_1$-$C_6$), phenylmethyl, cyclohexylmethyl, or

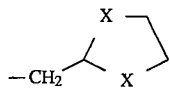

and A is

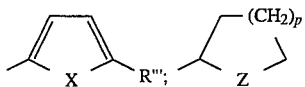

where Z is O, S, SO, $SO_2$, p is 1 or 2 and X is —O— or —S—.

In the Formula I, the asterisks denote asymmetric carbon atoms. The asymmetric center at the carbon attached to the $R_2$ substituent of the N-terminal unit may have the R or S configuration with the R configuration the most preferred.

DETAILED DESCRIPTION OF THE INVENTION

Within the group of compounds defined by Formula I, certain subgroups of compounds are preferred. Broadly preferred are those compounds where the α-amino acids have the natural L configuration. Especially preferred in the C-terminal units are compounds where the C-terminal units are selected from those of Formula II:

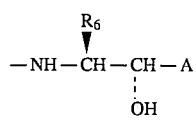

with an anti(threo) relationship between the amino group and the hydroxyl group. Most preferred of the 1-amino-2-hydroxy compounds of Formula II are those diastereomers with the 1S configuration.

Most preferred of the compounds of the Formula I are those wherein the C-terminal unit is represented by the Formula IIa:

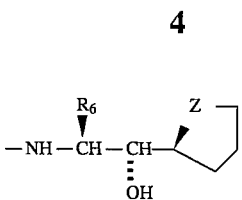

The products of Formula I and the preferred subgroups can be prepared by various synthetic procedures.

For example, the products can be prepared by reacting an N-protected e-aminoacid of Formula III:

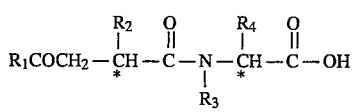

or its chemical equivalent with a 1-amino-2-hydroxy compound of Formula IV:

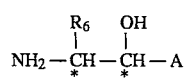

Thus, a compound of Formula III is reacted with a peptide coupling reagent to convert the carboxyl group into an activated derivative which is then reacted with a compound of Formula IV, or its chemical equivalent to give the products of this invention.

Preferred peptide coupling reagents are those which do not cause racemization at the carbons designated with asterisks. For example, appropriate peptide coupling reagents are:

1) N,N'-Dicyclohexylcarbodiimide plus 1-hydroxybenzotriazole
2) Benzotriazol-1-yloxytris (dimethylamino)phosphonium hexafluorophosphate (BOP-reagent)
3) N,N'-Bis[2-oxo-3-oxazolidinyl]phosphorodiamidic chloride (BOP-Cl)
4) Diphenylphosphinyl chloride (DPP-Cl)
5) Diethoxyphosphoryl cyanide
6) 2-Chloro-1-methylpyridinium iodide
7) Phenyl dichlorophosphate plus imidazole Other peptide coupling reagents which may be used include N,N'-dicyclohexylcarbodiimide, with or without N-hydroxysuccinimide, 1-benzotriazolyl diethyl phosphate, 1-chloro-N,N-2-trimethyl-propen-1-amine, diphenyl phosphoryl azide, diethyl phosphorochloridate, phenyl phosphorochloridate, N,N-carboxyldiimidazole, isobutyl chloroformate plus N-methylmorpholine.

In the compounds of Formula III, where $R_4$ is 4-imidazolylmethyl or (4-imidazolyl)$CH_2$X, the imidazole nitrogen may be blocked with an appropriate group such as tosyl, 2,4-dinitrophenyl, benzyl, or benzyloxymethyl, prior to coupling with compounds of Formula IV. A suitable blocking group is chosen so that conditions for its removal are compatible with other structural features in the product of Formula I.

Alternatively, an α-aminoacid derivative of Formula III is activated with an appropriate peptide coupling reagent and then reacted with a compound of Formula V in which the hydroxy group is protected with a removable blocking group Y. Suitable blocking groups are represented by trimethylsilyl, t-butyldimethylsilyl, tetrahydropyranyl, acetyl, benzoyl and the like. Removal of the hydroxyl blocking group then gives the compounds of Formula I:

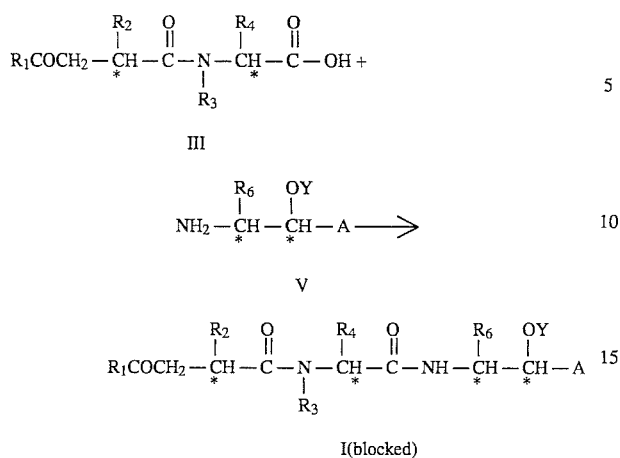

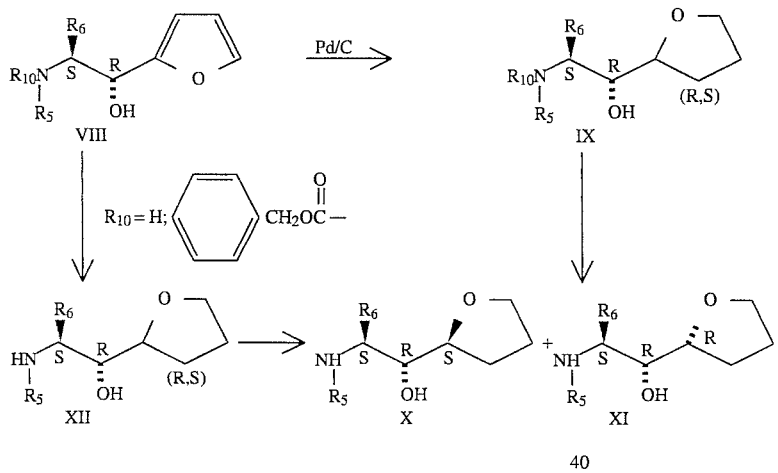

Derivatives of Formula VII lacking sulfur atoms in the $R_4$ and $R_6$ groups may be prepared by reduction of a compound of Formula VI:

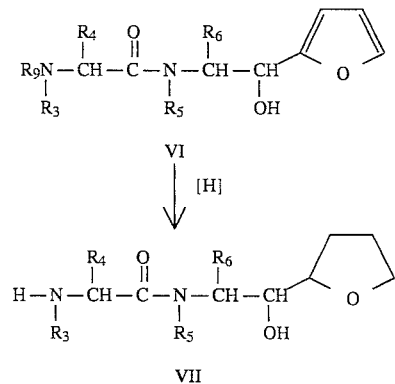

wherein $R_9$ is hydrogen or a blocking group such as benzyloxycarbonyl which is removed under hydrogenation conditions. If $R_9$ is a blocking group, such as tert-butoxycarbonyl, not removed under hydrogenation conditions, the group is removed in a separate step to give intermediates of Formula VII.

Intermediate 1-amino-2-hydroxy compounds of Formula X and XI are prepared by reduction of the furanyl group in compounds of Formula VIII. $R_{10}$ may be hydrogen or a suitable blocking group such as tert-butoxycarbonyl or benzyloxycarbonyl.

When $R_{10}$ is a benzyloxycarbonyl group, the blocking group is simultaneously removed during reduction of the furanyl group. The mixture of diastereomers XII may be separated to give the compounds X and XI or the blocked derivatives IX may be separated into the individual diastereomers and then deblocked to give intermediates X and XI.

Alternatively, the compounds of Formula I may be prepared by coupling N-blocked α-amino acids of Formula XIII (where $R_9$ is a removable blocking group such as tert-butoxycarbonyl, benzyloxycarbonyl and the like) to compounds of Formula V. The derivatives (Formula XIV) are then deblocked to give compounds of Formula XV which are coupled with the N-terminal unit to give compounds of Formula XVI (Scheme B). The hydroxyl blocking group (Y) is then removed to afford compounds of Formula I. The sequence of reactions may be carried out wherein the blocking group (Y) is removed first and the derivatives of Formula XVII, containing a free hydroxyl group are coupled to the N-terminal unit of formula XVIII. The coupling reactions (Scheme B) may also be carried out with the compounds of Formula V wherein the hydroxyl group is not blocked (Y=H) to give derivatives XIV(Y=H) and XV(Y=H).

Scheme B

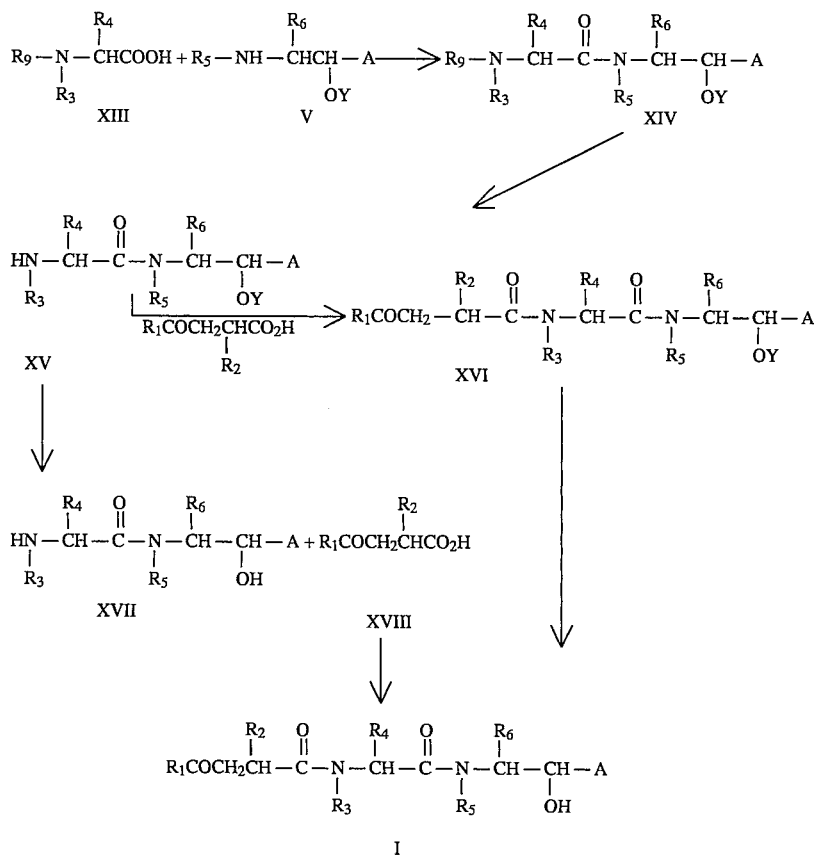

The compounds of Formula I are active inhibitors of renin.

Renin is an endopeptidase which plays an important role in the control of blood pressure. The renin angiotensin system is a multiregulated proteolytic cascade in which renin cleaves the protein substrate angiotensinogen to give angiotensin I. Angiotensin converting enzyme (ACE) catalyses the removal of the terminal dipeptide from the decapeptide angiotensin I to form angiotensin II which exhibits potent pressor activity.

Renin is an aspartyl protease with high substrate specificity and is the first proteolytic step in the renin-angiotensin system which is involved in the control of blood pressure.

Renin inhibitors have been shown to lower blood pressure in primates, [J. Hypertension, 1, 399 (1983), J. Hypertension 1 (suppl 2), 189 (1983)] and in man, [Lancet II, 1486 (1983), Trans. Assoc. Am. Physicians, 96, 365 (1983), J. Hypertension, 3, 653 (1985)] and thus are potentially useful in the control of hypertension.

The novel compounds of Formula I are new renin inhibitors and are useful in the treatment of hypertension in warm-blooded animals, as established in the following test.

Radioimmunoassay Screen For Renin Inhibitors

The in vitro method for the screening of anti-renin compounds involves, first, angiotensin I generation, and second, the quantitation of the angiotensin I produced by radioimmunoassay.

Angiotensin I Generation

The incubation medium consisted of 20 µl of purified human plasma angiotensinogen; (1) 10 µl of human kidney renin; (2) 5 µl of phenylmethylsulfonyl fluoride; 10 µl of disodium EDTA (10 mM); 10 µl of antirenin compound ($5\times10^{-3}$M, $5\times10^{-4}$M, $5\times10^{-5}$M) in dimethylformamide, or ethanol and a suitable amount of maleate buffer (77 mM, pH 6.0) to make a final volume of 500 µl. The reaction mixture is incubated for one hour at 37° C. and the enzymatic reaction is stopped by placing the tube in ice-cold water. The angiotensin I generated during the incubation is measured by a radioimmunoassay plasma renin activity kit (Clinical Assays, Inc.).

Radioimmunoassay Procedure

The incubation medium consisted of either 100 µl aliquots of the above reaction mixture or a standard amount of angiotensin I; 1000 µl of phosphate buffer (100 mM, pH 7.6) and 100 µl of ($^{125}$I) angiotensin in a gamma-coat tube. After three hours of incubation at room temperature, the tubes are decanted, and the radioactivity of each tube is determined in a gamma counter. Duplicate determinations are performed for each incubation. The results are expressed in ng of angiotensin I generated per ml of generation medium per hour of incubation (ng/AI/ml/hr).

The results of this test on representative compounds of this invention appear in Table I, expressed as an $IC_{50}$.

(1) The human plasma angiotensinogen derived from the blood of a woman receiving oral contraceptive pills is purified by chromatography on a pepstatinaminohexyl-agarose column.

(2) Human renin is prepared from human kidney.

TABLE I

Renin Inhibition

| Compound | IC$_{50}$ Molar Concentration |
|---|---|
| φ-CH$_2$-CO-CH(Ph)-CO-LeuNH-CH(Cy)-CH(OH)-CH$_2$-(furan) | $2.4 \times 10^{-8}$ |
| Ph-CO-CH$_2$-CH(Ph)-CO-LeuNH-CH(tetrahydropyranyl)-CH(OH)-CH$_2$-(tetrahydrofuranyl) | $2.7 \times 10^{-9}$ |
| (3-CF$_3$-Ph)-CO-CH$_2$-CH(Ph)-CO-LeuNH-CH(tetrahydropyranyl)-CH(OH)-CH$_2$-(tetrahydrofuranyl) | $3.3 \times 10^{-9}$ |
| φ-CH$_2$-CO-CH(Ph)-CO-HisNH-CH(tetrahydropyranyl)-CH(OH)-CH$_2$-(tetrahydrofuranyl) | $7 \times 10^{-11}$ |
| (furyl)-CO-CH$_2$-CH(Ph)-CO-LeuNH-CH(tetrahydropyranyl)-CH(OH)-CH$_2$-(tetrahydrofuranyl) | $1 \times 10^{-11}$ |
| (furyl)-CO-CH$_2$-CH(Ph)-CO-LeuNH-CH(tetrahydropyranyl)-CH(OH)-CH$_2$-(tetrahydrofuranyl) (diastereomer) | $1.9 \times 10^{-7}$ |
| Ph-CO-CH$_2$-CH(Ph)-CO-LeuNH-CH(Cy)-CH(OH)-CH$_2$-(thienyl) | $4.9 \times 10^{-7}$ |

TABLE I-continued

Renin Inhibition

| Compound | IC$_{50}$ Molar Concentration |
|---|---|
| (structure: thiazole–C(O)–CH$_2$–CH(naphthyl)–C(O)–LeuNH–CH(tetrahydropyranylmethyl)–CH(OH)–tetrahydrofuran) | $1.4 \times 10^{-7}$ |
| (structure: thiazole–C(O)–CH$_2$–CH(naphthyl)–C(O)–LeuNH–CH(tetrahydropyranylmethyl)–CH(OH)–cyclopentyl) | 33% inhibition at $10^{-5}$ |
| (structure: thiazole–C(O)–CH$_2$–CH(naphthyl)–C(O)–HisNH–CH(tetrahydropyranylmethyl)–CH(OH)–tetrahydrofuran, *R,S) | $1.4 \times 10^{-7}$ |
| (structure: phenyl–C(O)–CH$_2$–CH(phenyl)–C(O)–LeuNH–CH(cyclohexylmethyl)–CH(OH)–furan) | $4.0 \times 10^{-6}$ |
| (structure: phenyl–C(O)–CH$_2$–CH(phenyl)–C(O)–LeuNH–CH(cyclohexylmethyl)–CH(OH)–tetrahydrofuran) | $5.1 \times 10^{-8}$ |
| (structure: furan–C(O)–CH$_2$–CH(phenyl)–C(O)–HisNH–CH(cyclohexylmethyl)–CH(OH)–tetrahydrofuran) | $2.9 \times 10^{-8}$ |

TABLE I-continued

Renin Inhibition

| Compound | IC$_{50}$ Molar Concentration |
|---|---|
| [structure with furan, phenyl, HisNH, cyclohexyl, OH] | $8.6 \times 10^{-10}$ |
| [structure with furan, cyclohexyl, LeuNH, cyclohexyl, OH] | $5.1 \times 10^{-9}$ |
| [structure with furan, cyclohexyl, LeuNH, cyclohexyl, OH] | $1.6 \times 10^{-7}$ |
| [S-(R*,S*)]-1-cyclohexyl-2-[[2-[[1,4-dioxo-4-phenyl-2-(phenylmethyl)butyl]amino]-4-methyl-1-oxopentyl]amino]-4,7-epithio-1,2,4,5,6,7-hexadeoxy-L-arabino-Heptitol, (R and S)-S-oxide | IC50 $8.3 \times 10^{-9}$M |
| [S-(R*,R*)]4,7-anhydro-2-[[2-[[4-(2-benzofuranyl)-1,4-dioxo-2-(phenylmethyl)butyl]amino]-3-(1H-imidazol-4-yl)-1-oxopropyl]-amino]-1-cyclohexyl-1,2,5,6-tetradeoxy-L-arabino-Heptitol | IC50 $4.2 \times 10^{-8}$M |
| [S-(R*,S*)]-4,7-anhydro-2-[[2-[[4-(2-benzofuranyl)-1,4-dioxo-2-(phenylmethyl)butyl]amino]-3-(1H-imidazol-4-yl)-1-oxopropyl]amino]-1-cyclohexyl-1,2,5,6-tetradeosy-L-arabino-Heptitol | IC50 $1.5 \times 10^{-9}$M |
| [S-(R*,S*)]-4,7-anhydro-1-cyclohexyl-1,2,5,6-tetradeoxy-2-[[2-[[1,4-dioxo-2-(phenylmethyl)-4-(2-thienyl)butyl]amino]-4-methyl-1-oxo-pentyl]amino]-L-arabino-Heptitol | IC50 $8.0 \times 10^{-11}$M |
| [S-(R*,S*)]-1-cyclohexyl-1,2,4,5,6,7-hexadeoxy-2-[[2-[[1,4-dioxo-4-phenyl-2-(phenylmethyl)butyl]-amino]-4-methyl-1-oxopentyl]-amino]-4,7-epithio-L-arabino-Heptitol, [R (or S)]-S-oxide | IC50 $1.2 \times 10^{-8}$M |
| [S-(R*,R*)]-4,7-anhydro-1-cyclohexyl-1,2,5,6-tetradeoxy-2-[[4-methyl-2-[[4-[3-[(methylamino)-sulfonyl]phenyl]-1,4-dioxo-2-(phenylmethyl)buyhl]amino]-1-oxopentyl]amino]-L-arabino-Heptitol | IC50 $7.1 \times 10^{-8}$M |
| [S-(R*,S*)]-4,7-anhydro-1-cyclohexyl-1,2,5,6-tetradeoxy-2-[[4-methyl-2-[[4-[3-[(methylamino)-sulfonyl]phenyl]-1,4-dioxo-2-(phenylmethyl)butyl]amino]-1-oxopentyl]amino]-L-arabino-Heptitol | IC50 $2.4 \times 10^{-9}$M |
| [S-(R*,S*)]-4,7-anhydro-1-cyclohexyl-1,2,5,6-tetradoxy-2-[[2-[[1,4-dioxo-4-phenyl-2-(phenyl- | IC50 $4.7 \times 10^{-7}$M |

TABLE I-continued

Renin Inhibition

| Compound | IC$_{50}$ Molar Concentration |
|---|---|
| methyl)butyl]amino]-4-methyl-1-oxopentyl]amino]-D-xylo-Heptitol | |

The novel compounds of the present invention have been found to be highly useful for lowering elevated blood pressure in mammals when administered in amounts ranging from about 5 mg to about 50 mg/kg of body weight per day.

The compounds of this invention are preferably administered by a parenteral route such as intravenous, intramuscular or subcutaneous, but may be administered orally if desired.

Compositions, according to the present invention, having the desired clarity, stability and adaptability for parenteral use are obtained by dissolving from 0.10% to 10% by weight of active compound in a vehicle consisting of a polyhydric aliphatic alcohol or mixtures of such alcohols. Especially satisfactory are glycerin, propylene glycol and polyethylene glycols. Although various mixtures of polyethylene glycols may be used, it is preferred to use a mixture having an average molecular weight of from about 200 to about 400.

In addition to the active compound, the parenteral solutions may also contain various preservatives to prevent bacterial and fungal contamination as well as antioxidants to promote stability.

For intramuscular injection, the preferred concentration of active compound is 0.25 to 0.50 mg/ml of the finished compositions.

The novel compounds of this invention are equally adapted to intravenous administration when diluted with water or diluents employed in intravenous therapy such as isotonic glucose. For intravenous use, initial concentrations down to about 0.05 to 0.25 mg/ml of active compound are satisfactory.

The following specific examples illustrate the preparation of the compounds of this invention.

REFERENCE EXAMPLE 1

(S)2-Amino-3-cyclohexyl-(R)1-(2-furanyl)propan-1-ol

A. 1,1-Dimethylethyl (S)-[1-(cyclohexylmethyl)-2-(2-furanyl)-2-oxoethyl]carbamate A solution of 1.57 g of N-methoxy-N-methyl N$^\alpha$-t-butoxycarbonyl-L-cyclohexylalaninamide in 15 ml of dry tetrahydrofuran is cooled to −78° C. under argon. To the solution is added dropwise 5.9 ml of secondary butyllithium (0.85M in hexane). The viscous mixture is stirred at −78° C. for 1.5 hours and then warmed to 0° C. and stirred for 5 minutes. (Solution A)

A solution of 0.73 ml of furan in 5 ml of dry tetrahydrofuran is cooled to 0° C. and 3.8 ml of n-butyllithium (2.35M in hexane) added. The yellow suspension is stirred at 0° C. for 1.7 hours and then allowed to warm to room temperature for 15 minutes.
(yellow solution B)

The yellow solution B is added to solution A and the mixture stirred at 0° C. for 1.5 hours. The mixture is quenched with 5 ml of saturated aqueous ammonium chloride and the solvent tetrahydrofuran removed under vacuum. The residue is diluted with 50 ml of ethyl acetate and 20 ml of 1N hydrochloric acid. The organic phase is separated and washed successively with 20 ml of 1N hydrochloric acid, 20 ml of water, 20 ml of saturated sodium bicarbonate, 20 ml of brine and dried over sodium sulfate. The solvent is removed under vacuum to give 1.63 g of a light brown gum. This gum is dissolved in ether-hexane (1:5) and the solution filtered through a thin pad of hydrous magnesium silicate. The pad is washed with ether-hexane (1:5) and the filtrate concentrated. The residue is triturated with hexane to give 1.23 g of light yellow crystals; $[\alpha]_D^{26}+41°\pm1$ (c, 1.14, methanol).

B. (S)2-(N-tert-Butoxycarbonyl)amino-3-cyclohexyl-(R,S)1-(2-furanyl)propan-1-ol

A solution of 0.16 g of 1,1-dimethylethyl (S)-[1-(cyclohexylmethyl)-2-(2-furanyl)-2-oxoethyl]carbamate in 2 ml of dry tetrahydrofuran and 0.2 ml of methanol is cooled to 0° C. under argon and 23 mg of sodium borohydride added. The solution is stirred at 0° C. for one hour and quenched with 2 ml of saturated aqueous ammonium chloride. The organic solvent is removed under vacuum and the residue diluted with 5 ml of saturated aqueous ammonium chloride. The organic solvent is removed under vacuum and the residue diluted with 5 ml of water and extracted with 10 ml of ethyl acetate. The organic layer is separated, washed successively with 5 ml of 0.5N hydrochloric acid, 5 ml of saturated sodium bicarbonate, 5 ml of brine and dried over sodium sulfate. The solvent is removed under vacuum to give 0.19 g of gummy solid.

C. (4S-trans) 4-(Cyclohexylmethyl)-5-(2-furanyl)-2-oxazolidinone

To a solution of 0.23 g of (S)2-(N-tert-butoxycarbonyl)amino- 3-cyclohexyl-(R,S)1-(2-furanyl)propan-1-ol in 3 ml of dichloromethane is added 0.06 ml of trifluoroacetic acid. The solution is stirred for 23 hours at room temperature, washed with 1N sodium hydroxide, dried over sodium sulfate and the solvent removed to give 0.17 g of solid. This solid is dissolved in dichloromethane-ethyl acetate (9:1) and filtered through a thin pad of hydrous magnesium silicate. The filter pad is washed with two 10 ml portions of dichloromethane-ethyl acetate (9:1) and the filtrate and washes combined. The solvent is removed and residual solid washed with hexane to give 0.10 g of white crystals; $[\alpha]_D^{26}-124°\pm2$ (c, 0.417, CH$_3$OH).

D. (S)2-Amino-3-cyclohexyl-(R)1-(2-furanyl)propan-1-ol

A 0.15 g sample of (4S-trans) 4-(cyclohexylmethyl)-5-(2-furanyl)-2-oxazolidinone is dissolved in a mixture of 3 ml of ethanol and 3 ml of 1N sodium hydroxide. The solution is refluxed for 17 hours, diluted with 3 ml of water and concentrated under vacuum to remove the ethanol. The aqueous residue is extracted with two 5 ml portions of dichloromethane and the extracts dried over sodium sulfate. The solvent is removed to give 0.15 g of solid which is washed with hexane to give 0.13 g of white solid; $[\alpha]_D^{26}-10°\pm2$ (c, 0.507, methanol).

REFERENCE EXAMPLE 2

N-(L-leucyl)-(S)2-amino-3-cyclohexyl-(R)1-(2-furanyl)propan-1-ol

To a solution of 1.4 g of imidazole in 18 ml of dichloromethane is added 0.90 ml of phenyl dichlorophosphate in 6 ml of dichloromethane. The mixture is stirred for 20 minutes, cooled to 0° C. and a solution of 0.60 g of imidazole, 2.4 ml of N,N-dimethylformamide, and 1.60 g of N$^\alpha$-[(benzyloxy)carbonyl]-L-leucine in 6 ml of tetrahydrofuran added. The mixture is stirred at 0° C. for 40 minutes and then 1.30 g of (S)2-amino-3-cyclohexyl-(R)1-(2-furanyl)propan-1-ol added. The mixture is stirred at 0° C.–25° C. (ice bath allowed to melt) overnight and the solvent removed. The residue is dissolved in 20 ml of ethyl acetate and washed with water, 2N-citric acid, sodium bicarbonate solution and dried (MgSO$_4$). The solution is filtered through a thin pad of hydrous magnesium silicate (pad washed with several volumes of ethyl acetate). The filtrate is evaporated under vacuum to give 2.3 g of N-[N-(benzyloxy)carbonyl-L-leucyl]-(S) 2-amino-3-cyclohexyl-(R)1-(2-furanyl)propan-1-ol as an oil: RF=0.31 on thin layer chromatography (silica gel) with hexane-ethyl acetate (3:1) as solvent. The preceding compound (1.85 g) and 1.0 g of ammonium formate in 24 ml of methanol under nitrogen is warmed on a steam bath and then the solution chilled to 0° C. under nitrogen. To this mixture (without stirring) is added (by pipette) 0.96 g of 10% palladium on carbon suspended in 5 ml of ethanol. The mixture is chilled at 0° C. and stirred for 1 hour. Diatomaceous earth is added and the mixture filtered and the pad of diatomaceous earth washed with methanol. The filtrate is evaporated to dryness and the residue partitioned between ammonium hydroxide and dichloromethane. The organic layer is separated, dried (MgSO$_4$) and the solvent removed to give 1.24 g of gum. Crystallization from 5 ml of di-isopropyl ether gives 0.74 g N-(L-leucyl)-(S)2-amino-3-cyclohexyl-(R)1-(2-furanyl)propan-1-ol as colorless needles, m.p. 83°–84° C. $[\alpha]_D^{26}$ –17°±1 (c, 1 031, CH$_3$OH).

REFERENCE EXAMPLE 3

N-[N-(Benzyloxy)carbonyl-L-leucyl]-(S)-2-amino-3-cyclohexyl-(R)-1-(2-furanyl)propan-1-ol To a solution of 4.0 g of N-(benzyloxy)carbonyl-L-leucine (4.99 g) in 40 ml of dry tetrahydrofuran is added 3.05 g of N,N-carbonyldiimidazole. The solution is stirred at room temperature for 2.0 hours and then 4.0 g of (S)-2-amino-3-cyclohexyl-(R)-1-(2-furanyl)propan-1-ol is added. After stirring 5 hours under argon, the solvent is removed and the residue is dissolved in 80 ml of dichloromethane. The solution is washed twice with 40 ml of 2N citric acid, and with 40 ml of water, 1M sodium bicarbonate and brine to give an oil. Crystallization from diisopropyl ether gives 7.0 g of white crystals, m.p. 95°–97° C.: $[\alpha]_D^{26}$–39°±1 (c, 1,029, CH$_3$OH).

REFERENCE EXAMPLE 4

(S)-2-[(2-Amino-4-methyl-1-oxopentyl)amino]-4,7-anhydro-1-cyclohexyl-1,2,5,6-tetradeoxy-L-arabino-Heptitol and (S)-2-[(2-Amino-4-methyl-1-oxopentyl)amino]-4,7-anhydro-1-cyclohexyl-1,2,5,6-tetradeoxy-D-xylo-Heptitol N-[N-(benzyloxy)carbonyl-L-leucyl]-(S)-2-amino-3-cyclohexyl-(R)-1-(2-furanyl)propan-1-ol (7.0 g) is dissolved in 80 ml of methanol under argon and 6.12 g of ammonium formate added. To this mixture under argon is added a suspension of (10%) palladium on carbon (3.17 g) in 10 ml of water. The suspension is added from a pipette and an additional 2 ml of water used as a rinse of the pipette. After the addition, the solution is stirred and the temperature rose from 22° C. to 30° C. After stirring for 1 hour, 5 ml of water and 3 g of diatomaceous earth is added and the mixture filtered through a pad of diatomaceous earth. The filter pad is washed with methanol and the filtrate concentrated under vacuum until solid begins to separate. The mixture is acidified with 20 ml of 2N citric acid and extracted with three 40 ml portions of ether. The aqueous layer is made basic with concentrated ammonium hydroxide and extracted with three 80 ml portions of diethyl ether. The extract is dried (Na$_2$SO$_4$) and the solvent removed to give 3.7 g of an oil. The preceding oil (4.27 g) is chromatographed with a Waters-Prep 500 HPLC instrument (silica gel-two columns) with 1% triethylamine in ethyl acetate as solvent. Cuts containing the less polar component are combined, the solvent removed and the residue crystallized from diisopropyl ether to give 0,916 g of white crystals, m.p. 77°–78° C.: $[\alpha]_D^{26}$–25°±2 (c, 0.421, CH$_3$OH) (assigned D-xylo-diastereomer). Fractions containing the more polar component are combined, the solvent removed and the residue crystallized from diisopropylether to give 1.23 g of white crystals, m.p. 90°–92° C.: $[\alpha]_D^{26}$–26°±1 (c, 1.067, CH$_3$OH) (assigned L-arabino-diastereomer).

REFERENCE EXAMPLE 5

(S)-2-[(2-Amino-4-methyl-1-oxopentyl)amino]-4,7-anhydro-1-cyclohexyl-1,2,5,6-tetradeoxy-L-arabino-Heptitol and (S)-2-[(2-Amino-4-methyl-1-oxopentyl)amino]-4,7-anhydro-1-cyclohexyl-1,2,5,6-tetradeoxy-D-xylo-Heptitol Reduction of (L-leucyl)-(S)-2-amino-3-cyclohexyl-(R)-1-(2-furanyl)propan-1-ol with 10% palladium on carbon and ammonium formate as described in Reference Example 4 gives the products of the Example as a pair of diastereomers.

(a) white crystals, m.p. 77°–78° C.: $[\alpha]_D^{26}$–25° (c, 0.40, CH$_3$OH) (assigned D-xylo diastereomer).

(b) white crystals, m.p. 90°–92° C.: $[\alpha]_D^{26}$–26° (c, 1.0, CH$_3$OH) (assigned L-arabino diastereomer).

REFERENCE EXAMPLE 6

2-Amino-4,7-anhydro-1-cyclohexyl-1,2,5,6-tetradeoxy-L-arabino-Heptitol and 2-Amino-4,7-anhydro-1-cyclohexyl-1,2,5,6-tetradeoxy-D-xylo-Heptitol (S)-Amino-3-cyclohexyl-(R)-1-(2-furanyl)propan-1-ol (4.5 g) is dissolved in 110 ml of methanol under argon and 5.1 g of ammonium formate added. To this mixture is added a suspension of 10% palladium on carbon (2.25 g) in 5 ml of water (without stirring mixture). The suspension is added from a pipette and an additional 1 ml of water used as a rinse of the pipette. After the addition, the mixture is stirred and the temperature rose to 30° C. The mixture is stirred 2 hours and filtered through diatomaceous earth. The filter pad is washed with methanol and the filtrate concentrated to dryness. To the residue is added 50 ml of 1N sodium hydroxide and the mixture extracted with dichloromethane. The extract is dried (Na$_2$SO$_4$) and the solvent removed to give 3.3 g of an oil. This oil (2.8 g) is chromatographed on silica gel with a Waters-Prep 500 instrument with 2% triethylamine in ethyl acetate as solvent. Fractions containing the first compound eluted are combined and the solvent removed to give a solid. Sublimation gives 0.42 g of crystals, m.p. 74°–76° C. assigned 2-amino-4,7-anhydro-1 -cyclohexyl-1,2,5,6-tetradeoxy-D-xylo-Heptitol structure. The later fractions from the column are combined and the solvent removed to give 0.39 g of a solid, m.p. 81°–82° C., assigned 2-amino-4,7-anhydro-1-cyclohexyl-1,2,5,6-tetradeoxy-L-arabino-Heptitol structure.

REFERENCE EXAMPLE 7

N-(L-Histidyl)-(S)2-amino-3-cyclohexyl-(R)1-(2-furanyl)-propan-1-ol

To a mixture of 1.25 g of imidazole in 0.5 ml of dichloromethane is added 1.2 g of phenyl dichlorophosphate in 5 ml of dichloromethane. After stirring for 25 minutes, the mixture is chilled to 0° C. and to the mixture is added a warm solution of 1.65 g of $N^\alpha$-(benzyloxycarbonyl)-L-histidine and 0.55 g of imidazole in 2 ml of dry N,N-dimethylformamide. The mixture diluted to a volume of 10 ml with dichloromethane and stirred at 0° C. for I hour. To the mixture is added 1.25 g of (S)2-amino-3-cyclohexyl-(R)1-(2-furanyl)propan-1-ol and the mixture stirred overnight at 0° C. to 25° C. (ice bath allowed to melt). The mixture is concentrated under vacuum and the residue in 20 ml of ethyl acetate washed with 5 ml of water, three 5 ml portions of 1M sodium bicarbonate and brine. The organic layer was dried ($Na_2SO_4$) and the solvent removed to give 2.4 g of N-[N-(benzyloxycarbonyl)-L-histidyl](S)2-amino-3-cyclohexyl-(R)1-(2-furanyl)propan-1-ol as a gum. A mixture of the preceding gum (2.4 g), 1.52 g of ammonium formate, 0.37 ml of formic acid (90%) and 30 ml of methanol under nitrogen is chilled to 0° C. and then a slurry of 1.2 g of 10% palladium on carbon in ethanol was added by pipette. The cooled mixture was stirred 2.5 hours and filtered through diatomaceous earth. The filtrate is evaporated and to the residue is added 1 ml of concentrated ammonium hydroxide. The mixture is extracted successively with 10 ml, S ml and 5 ml portions of ethyl acetate. The combined extracts are dried ($Na_2SO_4$) and the solvent removed to give 1.2 g of a glass. This glass is chromatographed on silica gel column with solvent dichloromethane-methanol-triethylamine (94:6:2). Cuts containing product are combined, concentrated to dryness and partitioned between 10 ml of 2N ammonium hydroxide and 5 ml of dichloromethane. The organic layer is separated and the aqueous layer extracted with two 5 ml portions of dichloromethane. The organic layer and extracts are combined, dried ($Na_2SO_4$) and the solvent removed to give 0.22 g of solid: mass spec (FAB):found, 361 (M+H); calc., 361 (M+H).

REFERENCE EXAMPLE 8

2-[[2-Amino-3-(1-H-imidazol-4-yl)1-oxopropyl]amino-4,7-anhydro-1-cyclohexyl-1,2,5,6-tetradeoxy-L-arabino-(and D-xylo)Heptitol A mixture of 0.49 g of N-[N-(benzyloxycarbonyl)-L-histidyl]-(S)-2-amino-3-cyclohexyl-(R)-1-(2-furanyl)propan-1-ol and 0.68 g of ammonium formate in 6 ml of methanol is warmed to 60° C. and to the stirred mixture is added a suspension of 0.5 g of 10% palladium on carbon in 2.4 ml of ethanol. The mixture is stirred at 60° C. for 1.5 hours, diluted with 2 ml of water and filtered through diatomaceous earth. The filter cake is washed with ethanol and the filtrate concentrated. The aqueous residue is diluted with 0.4 ml of concentrated ammonium hydroxide and extracted with ethyl acetate. The extract is dried ($Na_2SO_4$) and the solvent removed to give 0.33 g of solid. This solid is again subjected to hydrogenation with 0.5 g of 10% palladium on carbon, 0.68 g of ammonium formate in 6 ml of methanol at 60° C. for 1.5 hours. Work up as previously describes gives 0.28 g of solid.

REFERENCE EXAMPLE 9

(S)2-tert-Butoxycarbonylamino-4-methyl-(R,S)1-(2-furanyl)pentan-1-ol

To 0.545 ml of furan in 10 ml of dry tetrahydrofuran under argon cooled to −20° C. is added 3.35 ml of 2.36M n-butyllithium in hexane. The solution is allowed to warm to 10° C. and stirred for 2 hours. The solution is chilled to −70° C. (dry ice-acetone) and 1.70 g of N-t-butoxycarbonyl leucinal in 10 ml of tetrahydrofuran is added. After I hour at −70° C., 10 ml of 10% ammonium chloride is added. The mixture is concentrated under vacuum, diluted with water and extracted with ether. The combined ether extracts are dried and concentrated. The residue is purified twice by thick layer chromatography on silica gel plates to give 0.20 g of product as a gum; RF 0.22 on thin layer chromatography (silica gel) with hexane-ethyl acetate (4:1) as solvent.

REFERENCE EXAMPLE 10

-[N-(Benzyloxycarbonyl)-L-histidyl]-(S)-2-amino-3-cyclohexyl-(R)-1-(2-furanyl)propan-1-ol Imidazole (2.2 g) is dissolved in 26 ml of dichloromethane and 2.06 g of phenyl dichlorophosphate in 8 ml of dichloromethane added. After stirring under argon for 10 minutes, the mixture is cooled to 0° C. and a solution of 2.82 g of $N^\alpha$-(benzyloxycarbonyl)-L-histidine, 0.94 g of imidazole in a mixture of 3.4 ml of N,N-dimethylformamide and 17 ml of dichloromethane is added. The mixture is stirred at 0° C. for 1 hour and a solution of 2.14 g of (S)-2-amino-3-cyclohexyl-(R)-1-(2-furanyl)propan-1-ol in 6 ml of dichloromethane added. The mixture is allowed to warm to room temperature over 5 hours and is stirred for 2 days. The mixture is concentrated under vacuum and diluted 100 ml of ethyl acetate. The mixture is washed with 1M sodium bicarbonate, and a solution of 1M citric acid-1M-sodium citrate and dried ($MgSO_4$). The solvent is removed to give 4.8 g of solid. This solid is chromatographed on silica gel by HPLC on a Waters-Prep 500A apparatus with ethyl acetate-methanol-triethylamine (96:2:2) as solvent. Cuts containing product are combined and the solvent removed under vacuum to give 2.54 g of solid: $[\alpha]_D^{26}$ −21°±1 (c, 0.732, $CH_3OH$) FAB (Mass Spectrum); Found M+H=495.

REFERENCE EXAMPLE 11 gamma-Oxo-alpha-(phenylmethyl)-3-(trifluoromethyl)benzenebutanoic acid

A sample of 1.714 g of sodium hydride (60% in oil) is washed with hexane under argon. To the solid sodium hydride is added 65 ml of dry tetrahydrofuran. To the mixture cooled to 0° C. is added dropwise 10.72 g of diethyl benzylmalonate. The mixture is stirred for 15 minutes and a solution of 11.44 g of 2-bromo-1-[3-(trifluoromethyl)phenyl]ethanone in 15 ml of tetrahydrofuran added dropwise. The ice bath is removed and the mixture stirred at room temperature overnight. The mixture is filtered and the filtrate concentrated under vacuum. The residue (19.3 g) is chromatographed by HPLC over silica gel on a Waters-Prep 500A instrument with hexane-ethyl acetate (10:1) as solvent to give 7.35 g of yellow oil. To the preceding compound (7.35 g) stirring in 30 ml of ethanol and 15 ml of water, while being cooled in an ice bath, is added slowly in several portions, 3.36 g of sodium hydroxide pellets. After 15 minutes, the ice bath is removed and the mixture is refluxed for 4 hours. The mixture is concentrated and the aqueous residue diluted with 35 ml of water, extracted with 20 ml of ether, and acidified with 6N hydrochloric acid (20 ml). The mixture is extracted with three 25 ml portions of dichloromethane, the extract dried ($Na_2SO_4$) and the solvent removed to give a yellow solid. The solid is dissolved in 45 ml of hexane-acetone (8:1) and the solution chilled to give 5.16 g of [2-oxo-2[3-(trifluoromethyl)phenyl]ethyl](phenylmethyl)propanedioic acid as white crystals, m.p. 145°–147° C. A solution of the preceding compound (4.88 g) in 50 ml of dioxane is refluxed for 4 hours and the solvent removed. The residue is crystallized from 20 ml of hexane to give 4.0 g of crystals which are recrystallized from hexane-ethyl acetate to give 3.35 g of white crystals, m.p. 90°–92° C. The following compounds may be prepared according to the procedure of Reference Example 11.

gamma-oxo-α-(phenylmethyl)benzenebutanoic acid, m.p. 163°–165° C.

3-chloro-gamma-oxo-α-(phenylmethyl)benzenebutanoic acid.

gamma-oxo-α-(phenylmethyl)-4-(3-trifluoromethyl)benzenebutanoic acid, m.p. 85°–89° C. 4-chloro-gamma-oxo-α-(phenylmethyl)benzenebutanoic acid.

3-(aminosulfonyl)-gamma-oxo-α-(phenylmethyl)benzenebutanoic acid.

3-[(4-morpholinyl)sulfonyl)]-gamma-oxo-α -(phenylmethyl)benzenebutanoic acid.

3-methyl-gamma-oxo-α-(phenylmethyl)-benzenebutanoic acid.

3-(methylaminosulfonyl)gamma-oxo-α-(phenylmethyl)benzenebutanoic acid, mp. 130°–133° C. gamma-oxo-alpha-(phenylmethyl)-2-benzofuranbutanoic acid, mp. 158°–161° C.

alpha-(cyclohexylmethyl)-gama-oxo-2-furanbutanoic acid, mp. 91°–94° C.

3,4-dimethoxy-gamma-oxo-α-(phenylmethyl)-benzenebutanoic acid.

3-(aminosulfonyl)-4-chloro-gamma-oxo-α-(phenylmethyl)benzenebutanoic acid.

3-(1-pyrrolidinylsulfonyl)-gamma-oxo-α-(phenylmethyl)benzenebutanoic acid.

3-(dimethylaminosulfonyl)-gamma-oxo-α-(phenylmethyl)benzenebutanoic acid.

3-(ethylaminosulfonyl)-gamma-oxo-α-(phenylmethyl)benzenebutanoic acid.

gamma-oxo-α-(phenylmethyl)-2-furanbutanoic acid, m.p. 140°–143° C.

gamma-oxo-α-(phenylmethyl)-2-thiophenebutanoic acid, mp. 168°–170° C.

5-chloro-gamma-oxo-α-(phenylmethyl)-2-thiophenebutanoic acid.

REFERENCE EXAMPLE 12

Methyl(R)-N-[1,4-dioxo-4-phenyl-2-(phenylmethyl)butyl]-L-leucinate

A mixture of 5.0 g of gamma-oxo-α-(phenylmethyl)benzenebutanoic acid and 3.02 g of N,N-carbonyldiimidazole and 125 ml of tetrahydrofuran under argon is stirred for 1.5 hours. To the solution is added 4.23 g of methyl L-leucinate hydrochloride and the mixture stirred overnight at room temperature. The mixture is filtered and the filtrate concentrated. The residue is diluted with S0 ml of ethyl acetate and the solution washed twice with 40 ml of 1N hydrochloric acid, once with 40 ml of 1M sodium bicarbonate, brine and dried (MgSO4). The filtrate is concentrated to dryness to give 5.7 g of white solid. This solid is chromatographed by HPLC on silica gel with a Waters-Prep 500A instrument to give 1.6 g of product (faster moving diastereomer). Crystallization from diisopropyl ether gives 1.1 g of white crystals, m.p. 66°–68° C.: $[α]_D^{26}$–15°±1 (c, 0.90, $CH_3OH$). Fractions containing the slower moving compound give 1.5 g of solid which is crystallized from diisopropyl ether to give 1.27 g of methyl (S)-N-[1,4-dioxo-4-phenyl-2-(phenylmethyl)butyl]-L-leucinate as white crystals, m.p. 81°–83° C.: $[α]_D^{26}$–65°±1 (c, 1.052, $CH_2OH$). The following compounds may be prepared according to the procedure of Reference Example 12.

Methyl(R)-N-[1,4-dioxo-4-[3-(trifluoromethyl)phenyl]-2-(phenylmethyl)butyl]-L-leucinate, m.p. 105°–107° C.

Methyl(S)-N-[1,4-dioxo-4-[3-(trifluoromethyl)phenyl]-2-(phenylmethyl)butyl]-L-leucinate, yellow oil.

Methyl(R)-N-[1,4-dioxo-4-[3-(aminosulfonyl)phenyl] -2-(phenylmethyl)butyl]-L-leucinate.

Methyl(R)-N-[1,4-dioxo-4-(3-chlorophenyl)-2-(phenylmethyl)-L-leucinate.

Methyl(R)-N-[1,4-dioxo-4-[3-(4-morpholinylsulfonyl)phenyl]-2-(phenylmethyl)butyl]-L-leucinate.

Methyl(R)-N-[1,4-dioxo-4-(4-chlorophenyl)-2-(phenylmethyl)butyl]-L-leucinate.

Methyl(R)-N-[4-(2-furanyl)-1,4-dioxo-2-(phenylmethyl)butyl]-L-leucinate, mp. 53°–55° C.

Methyl(R)-N-[1,4-dioxo-2-(phenylmethyl)-4-(2-thienyl)butyl]-L-leucinate.

Methyl(R)-N-[4-(5-chloro-2-furanyl)-14-dioxo-2-(phenylmethyl)butyl]-L-leucinate.

Methyl(R)-H-[2-(cyclohexylmethyl)-4-(2-furanyl)-1,4-dioxobutyl]-L-leucinate.

Methyl(R)-N-[a-(cyclohexylmethyl)-1,4-dioxo-4-(2-thienyl)butyl]-L-leucinate.

Methyl (S)-N-[4-(2-furanyl)-1,4-dioxo-2-(phenylmethyl)butyl]-L-leucinate, mp. 63°–65° C.

REFERENCE EXAMPLE 13

(R)-N-[1,4-dioxo-4-phenyl-2-(phenylmethyl)-butyl]-L-leucine

A mixture of 1.06 g of methyl(R)-N-[1,4-dioxo-4-phenyl-2-(phenylmethyl)butyl]-L-leucinate, 3 ml of methanol and 3 ml of 1N sodium hydroxide is stirred for one hour at room temperature. The mixture is washed on a steam bath for 0.5 hour. The mixture is concentrated to ½ volume and 4 ml of 1N hydrochloric acid added. Cooling and filtering gives a solid which is dissolved in dichloromethane, dried ($Na_2SO_4$)

and filtered through diatomaceous earth. The filter pad is washed with dichloromethane and the filtrate concentrated to give 0.86 g of solid: $[\alpha]_D^{26} -10° \pm 1$ (c, 1.02, $CH_3OH$).

REFERENCE EXAMPLE 14

(S)2-Amino-3-cyclohexyl-(R)1-(5-acetyl-2-furanal)-propan-1-ol

To a solution of 0.50 g of (4S-trans)4-(cyclohexylmethyl)-5-(2-furanyl)-2-oxazolidinone in 8 ml of n-butyllithium in hexane (2.2M). After 15 minutes, the solution is warmed to room temperature and N-methoxy-N-methyl acetamide in 1 ml of tetrahydrofuran is added. The mixture is stirred at room temperature for 3 hours and quenched with 4 ml of saturated ammonium chloride solution and 4 ml of water. The mixture is concentrated under vacuum to remove the tetrahydrofuran and then extracted with 20 ml of ethyl acetate. The extract is washed with 10 ml each of 1N hydrochloric acid, saturated sodium bicarbonate and brine. The organic layer is dried ($Na_2SO_4$) and the solvent removed to give 0.58 g of solid. Flash chromatography on silica gel with ethyl acetate-hexane (1:1) as solvent gives 0.29 g of (4S-trans)4-(cyclohexylmethyl)-5-(5-acetyl-2-furanyl)-2-oxazolidinone as a cream colored solid; $[\alpha]_D^{26} -116° \pm 1$ (c, 0.773, $CH_3OH$).

The preceding compound is dissolved in a mixture of 4 ml of ethanol and 4 ml of 1N sodium hydroxide and the solution heated at 80° C. for 6 hours. The solution is diluted with 4 ml of water, concentrated to remove the ethanol, and extracted twice with 8 ml of dichloromethane. The extract is dried ($Na_2SO_4$) and the solvent removed to give 0.11 g of solid. Flash chromatography on silica gel with 10% methanol in dichloromethane gives 85 mg of product as a yellow solid: $[\alpha]_D^{26} +64° +2$(c, 0.464, $CH_3OH$).

The following Reference Examples may be prepared by the procedure of Reference Example 14.

(S)-2-Amino-3-cyclohexyl-(R)-1-(5-acetyl-2-thienyl-)propan-1-ol.

(S)-2-Amino-3-cyclohexyl-(R)-1-(5-propionyl-2-furanyl-)propan-1-ol.

(S)-2-Amino-3-cyclohexyl-(R)-1-(5-propionyl-2-thienyl-)propan-1-ol.

REFERENCE EXAMPLE 15

4-[(3-Acetylphenyl)sulfonyl]morpholine

A solution of 20.02 g (0.1 mol) of 3-acetylbenzenesulfonyl fluoride and 29 ml of morpholine in 100 mL of THF is stirred at room temperature for 16 hours. The solvent is removed, the residue dissolved in $CH_2C_2$, and solution washed with $H_{2O}$ and 2N HCl. The organic layer is dried ($MgSO_4$), the solvent removed, and the residue crystallized from $CH_2Cl_2$-hexane to give 25.2 g (93%) of light yellow crystals, m.p. 144°–147° C.

The following compounds may be prepared by the procedure of Reference Example 15:

3-Acetylbenzenesulfonamide, m.p. 88°–89° C.
3-Acetyl-N-methylbenzenesulfonamide, m.p. 94°–95° C.
3-Acetyl-N-ethylbenzenesulfonamide, m,p. 68°–72° C.
1-[(3-acetylphenyl)sulfonyl]-pyrrolidine, m.p. 116°–118° C.

REFERENCE EXAMPLE 16

3-Acetyl-N,N-dimethylbenzenesulfonamide

To a solution of 40.44 g (0.20 mol) of 3-acetylbenzenesulfonyl fluoride in 200 ml of dry tetrahydrofuran is added 20.4 g (0.25 mol) of dimethylamine hydrochloride and 43.6 ml (0.25 mol) of N,N-diisopropylethylamine. The mixture is stirred at room temperature for 48 hours, diluted with 250 ml of 1N HCl and extracted with $CH_2Cl_2$. The extract is dried ($MgSO_4$) and the solvent removed. The residue is chromatographed (silica gel column) with $CH_2Cl_2$-hexane (1:1). The fractions containing product are combined, the solvent removed and the residue crystallized from $CH_2Cl_2$-hexane to give 28 g (62%) of white crystals, m.p. 73°–76° C.

Anal Calcd for $C_{10}H_{13}NSO_3$: C, 52.9;H,5.8;N,6.2;S,14.1. Found: C,52.9;H1H,5.8;N,6.3;S,13.7.

REFERENCE EXAMPLE 17

3-Acetyl-N,N-diethylbenzenesulfonamide

A solution of 40.4 g (0.20 mol) of 3-acetylbenzenesulfonyl fluoride, 32.2 g (0.44 mol) of diethylamine in 200 ml of dry tetrahydrofuran is stirred overnight at 23° C. and then refluxed for two days. Diethylamine (10 ml) is added and the solution refluxed for 24 hours and the solvent removed. The residue is dissolved in $CH_2Cl_2$ and the solution washed with 1NHCl and $H_2O$. The $CH_2Cl_2$ layer is dried ($MgSO_4$) and the solvent removed to give 45 g (88%) of thick oil. A sample is chromatographed (silica gel column) with $CH_2Cl_2$ to give a viscous oil.

Anal Calcd for $C_{12}H_{17}NSO_3$: C,56.5;H,6.7;N,5.5;S,12.6. Found: C,55.7;H,6.6;N,5.2;S,12.4.

REFERENCE EXAMPLE 18

Methyl (R)-N-[1,4-dioxo-4-phenyl-2-(phenylmethyl)butyl]-L-histidinate

A mixture of 1.3 g of gamma-oxo-alpha(phenylmethyl-)benzenebutanoic acid in 10 ml of tetrahydrofuran under nitrogen is added 0.81 g of N,N-carbonyldiimidazole. The solution is stirred for 1 hour, 0.36 g of imidazole added and then 1.2 g of methyl L-histidinate dihydrochloride added. The mixture is briefly heated, and then allowed to stir at room temperature overnight. The mixture is filtered and the filtrate concentrated under vacuum. The residue is dissolved in 20 ml of ethyl acetate and the solution washed with a solution of saturated sodium bicarbonate, a solution of 1M citric acid-0.5M sodium citrate (pH 4.5) solution and brine. The organic layer is dried ($Na_2SO_4$) and the solvent removed to give 1.2 g of a gum. A sample (0.100 g) is chromatographed on 20×20×0.2 cm thick layer silica gel plates to give 15 mg of the product of the Example as a gum.

$^1H$ NMR ($CDCl_3$) $\delta 3.70$(s,3,$OCH_3$), $\delta 4.73$(m,1) and 15 mg of a mixture of methyl (R,S)-N-[1,4-dioxo-4-phenyl-2-(phenylmethyl)butyl]-L-histidinate; 1H NMR ($CDCl_3$) $\delta 3.70$(s, 3,$OCH_3$), $\delta 4.73$(m,1) $\delta 3.65$(s,3,$OCH_3$), $\delta$ 4.63(m, 1). Chemical shifts are in ppm relative to internal tetramethylsilane.

The following compounds may be prepared according to the procedure of Reference Example 18.

Methyl (R)-N-[1,4-dioxo-4-[3-(trifluoromethyl)phenyl]-2-(phenylmethyl)butyl]-L-histidinate.

Methyl (S)-N-[1,4-dioxo-4-[3-(trifluoromethyl)phenyl]-

2-(phenylmethyl)butyl]-L-histidinate.

Methyl (R)-N-[1,4-dioxo-4-[3-(aminosulfonyl)phenyl]-2-(phenylmethyl)butyl]-L-histidinate.

Methyl (R)-N-[1,4-dioxo-4-(3-chlorophenyl)-2-(phenylmethyl)butyl]-L-histidinate.

Methyl (R)-N-[1,4-dioxo-4-[3-(4-morpholinylsulfonyl)phenyl]-2-(phenylmethyl)butyl]-L-histidinate.

Methyl (R)-N-[1,4-dioxo-4-(4-chlorophenyl)-2-(phenylmethyl)butyl]-L-histidinate.

Methyl (R)-N-[4-(2-furanyl)-1,4-dioxo-2-(phenylmethyl)butyl]-L-histidinate.

Methyl (R)-N-[1,4-dioxo-2-(phenylmethyl)-4-(2-thienyl)butyl]-L-histidinate.

Methyl (R)-N-[4-(5-chloro-2-furanyl)-1,4-dioxo-2-(phenylmethyl)butyl]-L-histidinate.

Methyl (R)-N-[2-(cyclohexylmethyl)-4-(2-furanyl)-1,4-dioxobutyl]-L-histidinate.

Methyl (R)-N-[2-(cyclohexylmethyl)-1,4-dioxo-4-(2-thienyl)butyl]-L-histidinate.

REFERENCE EXAMPLE 19

2-[[2-Amino-3-(1H-imidazol-4-yl)1-oxopropyl]amino]-4,7-anhydro-1-cyclohexyl-1,2,5,6-tetradeoxy-L-arabino-Heptitol To a mixture of 0.289 g of $N^{\alpha}$-(benzyloxycarbonyl)-L-histidine and 0.014 ml of triethylamine in 2 ml of N,N-dimethylformamide is added 0.44 g of benzotriazol-1-yloxytris(dimethylamino)phosphonium hexafluorophosphate (BOP). The mixture is stirred 1 minute and 0.200 g of 2-amino-4,7-anhydro-1-cyclohexyl-1,2,5,6-tetradeoxy-L-arabino-Heptitol added. The mixture is stirred overnight at room temperature and diluted with 5 ml of ethyl acetate. The mixture is washed three times with 1 ml of 2M sodium carbonate and with 1M citric acid-1M sodium citrate buffer and brine. The organic layer is concentrated to give 0.35 g of a foam. Chromatography on silica gel with dichloromethane-methanol-ammonium hydroxide (9:1.2:0.2) gives 0.30 g of a glass. To the preceding glass (0.30 g) and 0.4 g of ammonium carbonate in 7 ml of methanol under nitrogen is added a slurry of 10% palladium on carbon in 1.5 ml of water. The mixture is stirred for 1.5 hours, filtered through diatomaceous earth and the filter pad washed with methanol. The filtrate is concentrated. The residue in 1 ml of methanol and 0.2 ml of concentrated ammonium hydroxide is extracted four times with 5 ml portions of chloroform. The extracts are combined, dried ($Na_2SO_4$) and the solvent removed to give 0.19 g of solid: $[\alpha]_D^{26}$ $-24°+1$(c, 1.003, $CH_3OH$).

REFERENCE EXAMPLE 20

α-(2-Oxo-2-phenylethyl)-benzo[b]thiophene-3-propanoic acid

To a suspension of 6.42 g of pareformaldehyde in 76.5 g of acetic acid is bubbled in hydrogen chloride gas (8.66 g) until the solution becomes clear. To this mixture is added 20 g of benzo[b]thiophene over 5 minutes. The mixture is chilled at 4° C. overnight and then diluted with 300 ml of water. The mixture is extracted with three 100 ml portions of diethyl ether and the combined extract washed with water, sodium bicarbonate and dried ($Na_2SO_4$). The solvent is removed and the residue distilled (Kugelrour bulb to bulb) at 100° C. under a high vacuum to give 19.2 g of benzo[b]thien-3yl)methyl chloride as an oil.

To 70 ml of ethanol is added 2.47 g of sodium in small portions. To this solution is added 18.01 g of diethyl melonate and then 18.67 g of benzo[b]thien-3-yl)methyl chloride is added. The mixture is refluxed overnight and quenched with acetic acid, diluted with 200 ml of water and extracted with diethyl ether. The ether extract is washed with brine, dried ($Na_2SO_4$) and the solvent removed. The residue is chromatographed on silica gel with ethyl acetate-hexane (1:10) to give 15 g of diethyl (benzo[b]thien-3-yl)methylmalonate as an oil.

As described for Reference Example 11, the preceding compound is reacted with 2-bromoacetophenone and the product hydrolyzed with sodium hydroxide to give [2-oxo-2-[(phenyl)ethyl][(benzo[b]thien-3-yl)methyl]propanedioic acid. Refluxing in dioxane gives the product of the Example as a solid.

REFERENCE EXAMPLE 21

Alpha(cyclohexylmethyl)-gamma-oxo-2-furanbutanoic acid

To a solution of 50.0 g of diethyl benzylmalonate in 100 ml of methanol under nitrogen is added 5.0 g of 5% rhodium on alumina. The mixture is hydrogenated in a Parr hydrogenator at 50 pounds per square inch of hydrogen for 16 hours. The mixture is filtered through diatomaceous earth and the filtrate concentrated under vacuum to give 50.5 g of diethyl (cyclohexylmethyl)propanedioate as a colorless oil. A 2.80 g sample of sodium hydride (60% in oil) is washed with hexane (decanted) under argon and 70 ml of dry tetrahydrofuran added. The mixture is cooled in an ice bath and 17.94 g of diethyl (cyclohexylmethyl)propanedioate added dropwise over 15 minutes. To the mixture (0° C. to 5° C.) is added dropwise 13.23 g of 2-bromo-1-(2-furanyl)ethanone in 40 ml of tetrahydrofuran. The cooling bath is removed and the mixture stirred at room temperature overnight. The solvent is removed under vacuum and 100 ml of ether added. The mixture is filtered through 240 g of silica gel in a 600 ml glass sintered funnel and the silica gel pad washed with 2 liters of ether. The filtrate is concentrated to 300 ml and is washed three times with 100 ml portions of 1M sodium bicarbonate and with 100 ml of brine. The organic layer is dried (MgSO4) and the solvent removed to give 26.0 g of a brown oil. This oil is chromatographed on silica by HPLC on a Waters-Prep 500 instrument with hexane-ethyl acetate (12:1) to give 16 g of diethyl(cyclohexylmethyl)[2-(2-furanyl)-2-oxoethyl]-propanedioate as a light yellow oil.

To a solution of the preceding compound (15.14 g) in 80 ml of ethanol and 33 ml of water cooled in an ice bath is added in portions 8.31 g of sodium hydroxide. The mixture is stirred at room temperature overnight and concentrated. To the aqueous residue is added 80 ml of water and the solution extracted with three 45 ml portions of ether. The aqueous layer is chilled and acidified with cold 6N HCl. The mixture is extracted with dichloromethane (3×150 ml) and the extract concentrated. The residue is crystallized from a mixture of 40 ml of hexane and 15 ml of ethyl acetate to give 10.7 g of (cyclohexylmethyl)[2-(2-furanyl)-2-oxoethyl]propanedioic acid as off-white crystals, mp 127°–130° C.

A solution of the preceding compound (10.0 g) in 100 ml of dioxane is refluxed under argon for 4 hours and the solvent removed under vacuum. The residue is crystallized from a mixture of 20 ml of hexane and 5 ml of ethyl acetate to give 7.9 g of the title compound as white crystals, mp 91°–94° C.

The following compounds may be prepared according to the procedure of Reference Example 21 alpha(cyclohexylmethyl)-gamma-oxo-2-thiophene-butanoic acid.

alpha(cyclohexylmethyl)-gamma-oxo-4-(3-trifluoromethyl)benzenebutanoic acid alpha(cyclohexylmethyl)gamma-oxo-3-[(4-morpholinyl)sulfonyl]benzenebutanoic acid alpha(cyclohexylmethyl)gamma-oxo-3(methyl-aminosulfonyl)benzenebutanoic acid alpha(cyclohexylmethyl)gamma-oxo-3-(aminosulfonyl-4-chloro-benzenebutanoic acid alpha(cyclohexylmethyl)gamma-oxo-3-(dimethyl-aminosulfonyl)benzenebutanoic acid alpha(cyclohexylmethyl)gamma-oxo-3-(ethyl-aminosulfonyl)benzenebutanoic acid 5-chloro-alpha(cyclohexylmethyl)gamma-oxo-2-thiophenebutanoic acid 5-chloro-alpha(cyclohexylmethyl)gamma-oxo-2-furanbutanoic acid

REFERENCE EXAMPLE 22

1,1-Dimethylethyl (R)-beta-[[(S)4-(1-methylethyl)-2-oxo-3-oxazolidinyl]carbonyl]-1-naphthalenebutanoate To a solution of 10.0 g of (S)4-(1-methylethyl)-3-[3-(1-naphthalenyl)1-oxopropyl]-2 -oxazolidinone in 140.0 ml of dry tetrahydrofuran, cooled to −78° C., was slowly added 23.58 ml of a 1.5 molar solution of lithium diisopropylamide mono(tetrahydrofuran) in cyclohexane. The mixture was stirred for 30 minutes at −78° C. and then 15.6 ml of tert-butyl bromoacetate was added dropwise. The mixture was stirred at −78° C. for 30 minutes, at −15° C. for 3 hours and at 0° C. for one hour. The mixture was quenched with 50 ml of saturated ammonium chloride solution and extracted with dichloromethane. The extract was washed with water, brine, dried (MgSO$_4$) and the solvent removed. The residue was crystallized from hexane to give 7.06 g of white crystals; $[\alpha]_D^{26}$+95° (c, 1.03, CHCl$_3$).

REFERENCE EXAMPLE 23

(S)4-(1-Methylethyl)beta[(R)1-naphthalenylmethyl]-gamma-2-oxo-3-oxazolidinebutanoic acid To a solution of 3.0 g of 1,1-dimethylethyl(R)-beta-[[(S)4-(1-methylethyl)- 2-oxo-3-oxazolidinyl]carbonyl]-1-naphthalenebutanoate in 22.4 ml of dichloromethane, cooled to 0° C., was added 22.4 ml of trifluoroacetic acid. The mixture was allowed to warm to room temperature and was stirred for one hour. The mixture was concentrated under vacuum and to the residue was added 20 ml of saturated sodium bicarbonate. The aqueous layer was acidified with 5% hydrochloric acid and extracted with dichloromethane. The extract was washed with brine, dried (MgSO$_4$) and the solvent removed under vacuum to give a solid; $[\alpha]_D^{26}$+116° (c, 1.06, CHC1$_3$).

REFERENCE EXAMPLE 24

(R)-alpha-1-naphthalenylmethyl-gamma-oxo-2-thiazole butanode acid

To 7.05 g of (S)-4-(1-methylethyl)beta[(R)1-naphthalenylmethyl]-gamma-2-oxo-3-oxazolidinebutanoic acid in 10 ml of toluene under nitrogen is added 1.50 ml of oxalyl chloride. The mixture is warmed gently until gas evolution ceases. The solvent is removed under vacuum, toluene added and the solvent removed. The residue is dissolved in 10 ml of dichloromethane and 1.6 g of 2-trimethylsilylthiazole added. After stirring 2 hours the mixture is refluxed for 15 minutes and concentrated under vacuum. The residue is dissolved in 20 ml of ethyl acetate and the solution washed with three 10 ml portions of 1M sodium bicarbonate and dried (MgSO$^4$). The solution is filtered through hydrous magnesium silicate and the filter pad washed with ethyl acetate. The filtrate is concentrated under vacuum to give 2.67 g of a glass. Chromatography by HPLC on silica gel with Waters-Prep 500 instrument with hexane-ethyl acetate (3:1) gave 2.0 g of [S(R*,S*)]-4-(1-methylethyl)-3-[2-(1-naphthalenyl-methyl)-1,4-dioxo-4-2-thiazolyl)butyl]-2-oxazolidinone as a colorless glass: $[\alpha]_D^{26}$+84°± (c, 0,879, CH$_3$OH).

The preceding compound (2.0 g) is dissolved in 17 ml of tetrahydrofuran under nitrogen. To the solution, cooled to 0° C. is added 6 ml of water and 1.87 ml of 30% hydrogen peroxide. While chilling, a solution of 0.31 g of lithium hydroxide monohydrate in 9.2 ml of water is added (exotherm) slowly. After 1 hour is added a solution of 2.3 g of Na$_2$SO$_3$ in 14 ml of water and the mixture concentrated under vacuum and the aqueous residue extracted with 18 ml of dichloromethane. The aqueous layer is chilled (0° C.) and acidified with 6N hydrochloric acid and extracted with ethyl acetate (3×10 ml). The extract is dried (MgSO$_4$) and the solvent removed to give a glass. This glass is dissolved in 20 ml of 1M sodium bicarbonate and the solution extracted with dichloromethane. The aqueous layer is acidified with 3.5 ml of 6N HCl and extracted with ethyl acetate. The solvent is removed to give 1.24 g of a glass, mp 65°–90° C. This glass is dissolved in isopropyl acetate and filtered through a thin pad of hydrous magnesium silicate. The filter pad is washed with isopropyl acetate to give 0.92 g of the title product as a glass.

REFERENCE EXAMPLE 25

1,2,4,5,6,7-hexadeoxy-2-[[(1,1-dimethylethoxy)carbonyl]amino]-4,7-epithio-1 -phenyl-L-arabino (and D-xylo)-heptitol, S-oxide To a solution of 35.1 ml of dry diisopropylamine in 100 ml of tetrahydrofuran, chilled in an ice bath, under argon is added dropwise, 100 ml of n-butyllithium (2.4 molar) in hexane via syringe over 1 hour. To this solution is added dropwise 26.0 g of tetramethylene sulfoxide and the solution allowed to warm to room temperature (Solution A).

To a mixture of 13.3 g of N-tert-butoxycarbonyl-L-phenylalanine and 8.1 g of N,N-carbonyldiimidazole is added 100 ml of dry tetrahydrofuran. The mixture is stirred under argon until gas evolution ceases and for an additional 16 minutes (yellow solution B). The solution B is added in four separated portions via syringe to the stirred Solution A at room temperature. The mixture is stirred for 16 hours at room temperature and is quenched with 75 ml of saturated ammonium chloride solution. The mixture is filtered and the filtrate extracted with ethyl acetate and dichloromethane. The combined extracts are washed with saturated sodium chloride solution, dried (Na$_2$SO$_4$) and the solvent removed. The residue (24.4 g) is chromatographed on silica gel with a Waters-Prep 500 HPLC apparatus with ethyl acetate as solvent. Cuts containing product are combined and the solvent removed to give 5.15 g of [R-(R*,S*) and S-(R*,R*)]1,1-dimethylethyl[2-oxo-1-(phenylmethyl)-2-(tetrahydro-2-thienyl)ethyl] carbamate, S-oxide as a gum. $[\alpha]_D^{26}$–5°±1 (c, 1.075, CH$_3$OH); mass spectrum (CI) (MH$^+$=352).

Reduction of 0.20 g samples of the preceding compound with diisobutylaluminum hydride in tetrahydrofuran or lithium aluminum hydride in tetrahydrofuran or sodium borohydride in ethanol gives a gum as a mixture of diastereomers. The products of the example are separated by chromatography on silica gel with a Waters-Prep 500 apparatus with a mixture of ethyl acetate-hexane as solvent.

REFERENCE EXAMPLE 26

1-Cyclohexyl-1,2,4,5,6,7-hexadeoxy-2-[[(1,1-dimethylethoxy)carbonyl]amino]-4,7-epithio-L-arabino (and D-xylo)-Heptitol, S-oxide A solution of 15.6 ml of diisopropylamine in 50 ml of dry tetrahydrofuran under argon is cooled in an ice-methanol bath and 46 ml of n-butyllithium in hexane (2.5M) is added slowly. To this solution, cooled at 0° C., is added 10.4 ml of tetramethylenesulfoxide and then the mixture is allowed to warm to 25° C. (Mixture A).

A solution of 6.25 g of N-tert-butoxycarbonyl-L-phenylalanine and 3.72 g of N,N-carbonyldiimidazole in 50 ml of tetrahydrofuran is stirred under argon at room temperature for 0.5 hour and refluxed for 0.5 hour and then chilled. (Solution B) The solution B is added over 15 minutes via double needle technique under nitrogen to the mixture A while cooling. The mixture is stirred for 3 hours and quenched with 50 ml of saturated aqueous ammonium chloride and 100 ml of ethyl acetate added. The organic layer is separated and washed with 1M sodium bicarbonate solution, 2M aqueous citric acid solution and 50 ml of brine. The organic layer is dried (Na$_2$SO$_4$) and the solvent removed to give 8 g of yellow oil. This oil is chromatographed on silica gel by HPLC on a Waters-Prep 500 apparatus with hexane-ethyl acetate (9:1) as solvent. The major brood fraction containing two major components by thin layer chromatography (silica gel-with 9:1 hexane-ethyl acetate) is collected and the solvent removed to give 1,1-dimethylethyl [R-(R*,R*) and S-(R*,R*)][2-oxo-1-(cyclohexylmethyl)-2-(tetrahydro-2-thienyl)ethyl] -carbamate, S-oxide as a gum: $[\alpha]_D^{26}$–11°±1 (c, 0.774, CH$_3$OH);

The preceding compound (0.5 g) is dissolved in 5 ml tetrahydrofuran and added to a mixture of sodium borohydride in 5 ml of tetrahydrofuran cooled to −78° C. The mixture is stirred 2 hours at −78° C. and 2 hours at room temperature and quenched with aqueous ammonium chloride, the mixture is then concentrated, extracted with ethyl acetate and the extract dried (Na$_2$SO$_4$). The solvent is removed to give the title product as a gum.

REFERENCE EXAMPLE 27

1,1-Dimethylethyl[1-cyclohexylmethyl)-2-hydroxy-2-(tetrahydro-2H-pyran-2-yl)ethyl]-carbamate A solution of 1,582 g of 2-(phenylsulfonyl)tetrahydropyran in 20 ml of tetrahydrofuran is cooled in a dry ice acetone bath and 4.7 ml of a solution of n-butyllithium in hexane (1.5M) is added. After stirring for 15 minutes 0,638 g of N-tert-butylcarbonyl-L-3-(cyclohexyl)alanal in 5 ml of tetrahydrofuran is added and the mixture stirred at −78° C. for 15 minutes. The mixture is allowed to warm to 0° C. over a period of hours and a solution of 25 ml of saturated sodium bicarbonate is added. The mixture is extracted with two 100 ml portions of ether, the extract washed with saturated sodium chloride solution, dried (Na$_2$SO$_4$) and the solvent removed under vacuum to give 1.30 g of 1,1-dimethylethyl [1-(cyclohexylmethyl)-2-(5,6-dihydro-4H-pyran-2-yl)-2-hydroxyethyl]-carbamate as a light yellow oil.

A 1.13 g sample of the preceding compound is dissolved in 10 ml of methanol and 0.66 g of ammonium formate added. To the mixture under argon is added a slurry of 0.39 g of 10% palladium on carbon in 5 ml of water. The mixture is stirred for 6 hours and filtered through diatomaceous earth. The filter pad is washed with methanol and the filtrate concentrated under vacuum. The mixture is extracted with two 50 ml portions of ethyl acetate and the extract washed with saturated sodium chloride solution. The organic layer is dried (Na$_2$SO$_4$) and the solvent removed under vacuum to give the title compound as a pale yellow gum.

REFERENCE EXAMPLE 28

2-[[2-amino-3-(1H-imidazol-4-yl)-1-oxo-propyl]amino]4,7-anhydro-1-cyclohexyl-1,2,5,6-tetradeoxy-L-arabino (and D-xylo)-Heptitol (1:1 mixture of diastereomers)

To a mixture of 6.65 g of N$^\alpha$-benzyloxycarbonyl-L-histidine in 45 ml of dry N,N-dimethylformamide under nitrogen is added 0.32 ml of triethylamine. To the mixture is added 11.1 g of benzotriazol-1-yloxytris(dimethylamino-)phosphonium hexafluorophosphate (BOP). After 1minute is added 4.54 g of a mixture of 2-amino-4,7-anhydro-1-cyclohexyl-1,2,5,6-tetradeoxy-L-arabino (and D-xylo)-Heptitol (1:1 mixture of diastereomers) in 5 ml of N,N-dimethylformamide. The mixture is stirred at room temperature for 2 days and then concentrated under vacuum. The residue is dissolved in 100 ml of ethyl acetate and the solution washed with 1M sodium carbonate, 1M citric acid -1M-sodium citrate buffer, brine and dried (Na$_2$SO$_4$). The filtrate is concentrated under vacuum. The residue is chromatographed on silica gel by HPLC with a Waters-Prep 500 instrument with ethyl acetate-methanol (4:1) containing 2% triethylamine. The combined product fractions are concentrated under vacuum to give 7.3 g of solid.

To a sample (7.18g) of the preceding compound and 9.1 g of ammonium formate in 160 ml of methanol under argon is added (without stirring) a suspension of 3.7 g of 10% palladium on carbon in 35 ml of water. The mixture is stirred (without cooling) for 1 hour. Diatomaceous earth which had been washed with water is added and the mixture filtered through diatomaceous earth. The filter pad is washed with methanol and the filtrate concentrated. The aqueous residue is made basic with concentrated ammonium hydroxide and extracted with ethyl acetate. The extract is dried (Na$_2$SO$_4$) and the solvent removed to give 3.85 g of the title compound as a glass (Ca 90% pure by pmr analysis): $[\alpha]_D^{26}$−20°±1 (c, 1.06, CH$_3$OH);

REFERENCE EXAMPLE 29

Methyl (R)-N-[4-(2-Furanyl)-1,4-dioxo-2-(phenylmethyl)-butyl]-L-histidinate and Methyl (S)-N-[4-(2-Furanyl)-1,4-dioxo-2-(phenyl-methyl)butyl]-L-histidinate To a solution of 3.7 g of gamma-oxo-α-(phenylmethyl) 2-furanbutanoic acid in 70 ml of tetrahydrofuran is added 1.57 ml of 4-methylmorpholine and the solution cooled to −10° C. To the solution is added 1.86 ml of isobutyl chloroformate. After stirring 1 minute, a mixture of 3.15 ml of 4-methylmorpholine and 3.47 g of methyl histidinate dihydrochloride in 15 ml of tetrahydrofuran is added. The mixture is stirred at room temperature overnight and the solvent removed. The residue is diluted with 150 ml of ethyl acetate. The solution is washed with 50 ml of water, 50 ml of 1N sodium bicarbonate, dried ($Na_2SO_4$) and the solvent removed to give 3.92 g of solid.

The preceding solid is chromatographed on silica gel by HPLC with a Waters-Prep-500 instrument (2-columns) with dichloromethane-triethylamine-methanol (48:1:1) as solvent. Cuts 9–12 (one spot by TLC) are combined, and the solvent is removed. The residue is dissolved in ethyl acetate and the solution washed with three 20-ml portions of brine, dried ($Na_2SO_4$) and the solvent removed to give 0.62 g of methyl(R)-N-[4-(2-furanyl)-1,4-dioxo-2-(phenylmethyl)butyl]-L-histidinate as a glass; $[\alpha]_D^{26}+6°\pm1$ (c, 0.893, $CH_3OH$). Fractions 15–20 are combined and the solvent is removed. The residue is dissolved in ethyl acetate (50 ml) and the solution washed with three 20 ml portions of brine, dried ($Na_2SO_4$) and the solvent removed to give 0.45 g of methyl (S)-N-[4-(2-furanyl)-1,4-dioxo-2-(phenylmethyl)butyl]-L-histidinate as a white foam: $[\alpha]_D^{26}-31°\mp1$ (c, 0.97 1, $CH_3OH$);

REFERENCE EXAMPLE 30

4,7-Anhydro-2-(carboxyamino)-1,2,5,6-tetradeoxy-1-cyclohexyl-L-arabino (and D-xylo)-Heptitol intramol 2,3 -ester A solution of 50 mg (0.2 mmol) of (48-trans)-4-(cyclohexylmethyl)-5-(2-furanyl)-2-oxazolidinone in ethyl acetate (4 ml) is hydrogenated at 25 psi, at room temperature, in the presence of 80 mg of 5% rhodium on alumina for 4 hours. The mixture is then filtered through diatomaceous earth and the filter pad is washed with 6 ml of ethyl acetate. The filtrate is washed with 5 ml of 1N hydrochloric acid and 5 ml of brine, dried over anhydrous sodium sulfate, and evaporated. The residue is triturated with a small amount of hexane to give 45 mg of a white solid (a mixture of two diastereomers in about 121 ratio). A 10 g sample of the preceding compound is hydrogenated in a similar manner to give 7.5 g of white solid. Chromatography of 8.5 g on silica gel by HPLC on a Waters-Prep 500 instrument with hexane-ethyl acetate (3:1) as solvent gives 4.05 g of L-arabino diastereomer as white crystals, mp 93°–96° C. and 2.3 g of D-xylo diastereomer as white crystals, mp 143°–145° C.

REFERENCE EXAMPLE 31

2-Amino-4,7-anhydro-1-cyclohexyl-1,2,5,6-tetradeoxy-L-arabino-Heptitol

To a solution of 0.70 g of 4,7-anhydro-2-(carboxyamino)-1-cyclohexyl-1,2,5,6-tetradeoxy-L-arabino-heptitol, intramol-2,3-ester in ethanol (14 ml) is added with stirring 14 ml of 1N sodium hydroxide. The mixture is heated at 70° C. for 16 hours. The ethanol is evaporated and the aqueous residue is extracted with 3×100 ml of methylene chloride. The combined extracts are dried over anhydrous sodium sulfate, and evaporated to give 0.63 g of a white solid, $[\alpha]_D^{26}-19°\pm1$ (c, 1.089, MeOH).

REFERENCE EXAMPLE 32

N-Methoxy-N-methyl-$N^\alpha$-t-butoxycarbonyl-L-phenylalaninamide

To a solution of 44.2 g (0.65 mole) of imidazole in methylene chloride (300 ml) is added with stirring 19.4 ml (0.13 mole) of phenyldichlorophosphate. The mixture is stirred at room temperature for 0.5 hour, and then cooled to 0° C. A solution of 34.5 g (0.13 mole) of N-t-butoxycarbonyl-L-phenylalanine in 10 methylene chloride (120 ml) is added, and the mixture is stirred at 0° C. for 1 hr. N,O-dimethylhydroxylamine hydrochloride (15.2 g, 0,156 mole) is then added in small portions. The resulting mixture is stirred at 0° C. for 5 hours and at room temperature for 16 hours. The final suspension is diluted with 400 ml of methylene chloride, washed with 1N hydrochloric acid (2×200 ml), water (200 ml), saturated potassium carbonate solution (200 ml), and brine (200 ml), and dried over anhydrous magnesium sulfate. Removal of solvents gives 40.2 g of the title compound as a pale yellow oil, $[\alpha]_D^{26}+22°\pm1$ (c, 1.052, $CHCl_3$).

REFERENCE EXAMPLE 33

1,1-Dimethylethyl-(S)-[1-phenyl-2-(2-furanyl)-2-oxoethylcarbamate

The title compound is prepared in a similar manner as Reference Example 1(A), using N-methoxy-N-methyl $N^\alpha$-t-butoxycarbonyl-L-phenylalaninamide as starting material. $[\alpha]_D^{26}70°\pm1$ (c, 1.024, MeOH).

REFERENCE EXAMPLE 34

(S)-2-(N-t-Butoxycarbonyl)amino-3-phenyl-(R,S)-1-(2-furanyl)propan-1-ol

The title compound is prepared in a similar manner as Reference Example 1(B), using 1,1-dimethylethyl-(S)-[1-phenyl-2-(2-furanyl)-2-oxoethyl] carbamate as starting material. $[\alpha]_D^{26}-24°\pm1$ (c, 1.152, MeOH).

REFERENCE EXAMPLE 35

(4S-trans)-4-phenylmethyl-5-(2-furanyl)-2-oxazolidinone

The title compound is prepared in a similar manner as Reference Example 1(C), using (S)-2-(N-t-butoxycarbonyl)amino-3-phenyl-(R,S)-1-(2-furanyl)propan-1-ol as starting material. $[\alpha]_D^{26}-1220°\pm1$ (c, 1.003, MeOH).

REFERENCE EXAMPLE 36

4,7-Anhydro-2-(carboxyamino)-1,2,5,6-tetradeoxy-1-phenyl-L-arabino (and D-xylo)-Heptitol, intramol. 2,3-ester A solution of 4.0 g (16 mmol) of (4S-trans)-4-phenyl-5-(2-furanyl)-2-oxoazolidinone is hydrogenated at 30 psi, in the presence of 1.0 g of 5% rhodium on alumina, for 6 hours. The mixture is filtered through diatomaceous earth, and the filter pad eluted with 20 ml of ethyl acetate. The filtrate is washed with 2×15 ml of 1N hydrochloric acid, and 15 ml of brine, dried over anhydrous sodium sulfate, and evaporated to give 3.02 g Of a beige solid. The crude solid is chromatographed with silica gel (230–400 mesh), and ethyl acetate-methylene chloride (1:5) as the eluting solvent, yielding:

A. 1.41 g of 4,7-anhydro-2-(carboxyamino)-1,2,5,6-tetradeoxy-1-phenyl-L-arabino-Heptitol, intramol. 2,3-ester as a white solid, $[\alpha]_D^{26}$ −62°±1 (c, 1.010, $CHCl_3$).

B. 0.90 g of 4,7-anhydro-2-(carboxyamino)-1,2,5,6-tetradeoxy-1-phenyl-D-xylo-Heptitol, intramol. 2,3-ester as white needles, $[\alpha]_D^{26}$ −107°±1 (c, 0.986, $CHCl_3$).

REFERENCE EXAMPLE 37

4,7-Anhydro-2-(carboxyamino)-1,2,5,6-tetradeoxy-1-cyclohexyl-L-arabino-Heptitol, intramol. 2,3-ester A mixture of 0.74 g (3 mmol) of 4,7-anhydro- 2-(carboxyamino)-1,2,5,6-tetradeoxy-1-phenyl-L-arabino-Heptitol, intramol. 2,3-ester and 0.30 g of 5% rhodium on alumina in methanol (30 ml) is hydrogenated at 25 psi for 4 hours. The mixture is filtered through diatomaceous earth and the filtrate is evaporated. The residue is triturated with hexane to give 0.76 g of a white solid, $[\alpha]_D^{26}$ −73°±1 (c, 0.98, MeOH).

REFERENCE EXAMPLE 38

(R)-N-[4-(2-Furanyl)-1,4-dioxo-2-(phenylmethyl)-butyl]-L-histidine

A mixture of 0,581 g of methyl (R)-N-[4-(2-furanyl)-1, 4-dioxo-2-(phenylmethyl)butyl]-L-histidinate, 1.8 ml of methanol and 1.8 ml of 1N sodium hydroxide is stirred at room temperature for 2 hours. The solvent is removed, water added and the pH adjusted to pH 4 to pH 5. The mixture is extracted with dichloromethane (5×10 ml), the extract dried ($Na_2SO_4$) and the solvent removed to give 0.26 g of product as a white foam. The aqueous layer is extracted again with ethyl acetate (3×10 ml) and with chloroform containing 1% $CH_3OH$. The ethyl acetate and chloroform extracts are combined, dried ($Na_2SO_4$) and the solvent removed to give 0.21 g of product as a white foams $[\alpha]_D^{26}$ +25°±1 (c, 0.92, $CH_{30}H$).

REFERENCE EXAMPLE 39

2-Amino-1-cyclohexyl-1,2,4,5,6,7-hexadeoxy-4,7-epithio-L-arabino-Heptitol

To a solution of 0.1 g of 4,7-anhydro-2-(carboxyamino)-1-cyclohexyl-1,2,5,6-tetradeoxy-D-xylo-Heptitol in 1 ml of dichloromethane is added 1 ml of 1M borontribromide in dichloromethane. The mixture is stirred at room temperature for 16 hours, water (2 ml) is added and the dichloromethane allowed to evaporate. The mixture is filtered to give 0.114 g of crystals, mp. 117°–121° C. Recrystallization from dichloromethanediisopropylether gives 0.094 g of [4S-[4α, 5β(S*)]]-5-(4-bromo-1-hydroxybutyl)-4-(cyclohexylmethyl)-2-oxazolidinone as needles, top. 124°–125° C.; $[\alpha]_D^{26}$ −64°±1 (c, 1.0 18, $CH_3OH$).

The preceding compound (0,222 g) and 0,103 g of potassium thioacetate in 2 ml of acetonitrile is stirred overnight. The mixture is diluted with 10 ml of water and filtered to give 0.193 g of crystals, mp. 107°–108° C. Recrystallization from dichloromethane-diisopropyl ether gives 2-(carboxyamino)-1-cyclohexyl-1,2,5,6-tetradeoxy-7-thio-D-xylo-Heptitol, 7-acetate, intramol. 2,3-ester as crystals, mp. 108°–109° C.; $[\alpha]D^{26}$ −60°±1 (c, 1.00, $CH_3OH$).

To the preceding compound (2.85g) in 16 ml of dichloromethane (cooled to 0° C.) is added 1.8 ml of dry triethylamine and 1.0 ml of methanesulfonyl chloride. The mixture is stirred for one hour diluted with 40 ml of dichloromethane and 16 ml of water. The organic layer is separated and the aqueous layer extracted with dichloromethane. The organic layer and extracts are combined, dried and the solvent removed to give 3.6 g of crystals, mp. 143°–153° C. Recrystallization from diisopropyl ether gives 0.41 g of 2-(carboxyamino)-1-cyclohexyl-1-1,2,5,6-tetradeoxy-7-thio-D-xylo-Heptitol, 7-acetate, 4-methanesulfonate, intramol. 2,3-ester as crystals, mp. 163°–164° C.; $[\alpha]D^{26}$ −45°±1 (c, 1.0, $CHCL_3$).

Analytical talc. for $C_{17}H_{29}NO_6S_2$: c, 50.1; H, 7.2; N, 3.4; S, 15.7. Found: C, 49.6; H, 7.1; N, 3.0; S, 15.1.

The preceding compound (42 mg) in 0.8 ml of dichloromethane and 0.2 ml of methanol is added 0.048 g of cesium carbonate. After 2 hours, water (0.7 ml) is added and the organic layer separated. The aqueous layer is extracted with dichloromethane and the organic layer and extracts combined. The extract is dried ($MgSo_4$) and the solvent removed to give 25 mg of 2-(carboxyamino)-1-cyclohexyl-1,2,4,5,6,7-hexadeoxy-4,7-epithio-L-arabino-Heptitol, intramol. 2,3-ester as crystals, mp. 118–119° C. A solution of the preceding compound (0.23 g) and 4.2 ml of 1M sodium hydroxide in 4.2 ml. of ethanol is refluxed overnight. The solution is concentrated to ½ volume and the oil which separates crystallized. The aqueous layer is extracted with dichloromethane and the organic layer separated and the solvent removed to give crystals. The two batches of crystals are combined and sublimed to give 0.115 g of 2-amino-1-cyclohexyl1,2,4,5,6,7-hexadeoxy-4,7-epithio-L-arabino-Heptitol as crystals, mp. 58°–59° C.; $[\alpha]_D^{26}$ +50°±1 (c, 1.00, $CH_3OH$).

REFERENCE EXAMPLE 40

(S)-2-Amino-4-methyl-(R)-1-(2-thienyl)pentan-1-ol

A 0,81 g portion of (S)-2-(tert-butoxycarbonyl) amino-4-methyl-(R,S)-1-(2-thienyl)pentan-1-ol was dissolved in 5 ml of dichloromethane and 2.1 ml of trifluoroacetic acid added, this mixture was stirred for 3 hours, then poured with stirring into 15 ml of ice-cold 2N sodium hydroxide. The mixture was diluted with 25 ml of dichloromethane, the organic layer separated and the aqueous layer extracted with 20 ml of dichloromethane. The organic layer and extract were combined, washed with saturated sodium chloride solution, dried and the solvent removed in vacuo. The residue was chromatographed on a silica gel column with ethyl acetate= hexane (1:4), giving 0.72 g of (4S-trans)-4-(2-methylpropyl)-5-(2-thienyl)-2 -oxazolidinone as a white solid $[\alpha]_D^{26}$ −141°±2 (c, =0.570, methanol).

A 0.23 g portion of the above solid was dissolved in 5 ml of ethanol and 5 ml of 1N sodium hydroxide added. The solution was refluxed for 16 hours and then concentrated in vacuo. The residue was extracted with two 10 ml portions of dichloromethane. The extracts were combined, dried and the solvent removed in vacuo, giving 0.2 g of the desired compound; Rf 0.045 [silica gel; ethyl acetate:hexane (1:2)].

REFERENCE EXAMPLE 41

(S)-2-Amino-3-cyclohexyl-(R)-1-(2-thienyl)propan-1-ol

To a solution of 1.57 g of N-methoxy-N-methyl $N^\alpha$-t-butoxycarbonyl-L-cyclohexylalaninamide in 10 ml of diethyl ether, cooled to −78° C., was added under argon 2.1 ml of 2.35M n-butyllithium in hexane. After stirring for one hour, the mixture was allowed to warm to 0° C. To this was added a solution of 2-lithiothiophene in ether (prepared from 0.64 g of thiophene in 5 ml of ether and 3.2 ml of 3.25M n-butyllithium in hexane at 0° C. for one hour). This mixture was stirred at 0° C. for 2 hours, then quenched with 15 ml of 1N hydrochloric acid and diluted with 25 ml of ether. The organic layer was separated, washed successively with ml of 1N hydrochloric acid, 10 ml of water and 15 ml of saturated sodium bicarbonate, dried and filtered through a short pad of hydrous magnesium silicate. The filter pad was washed with ether, the filtrate and wash combined and evaporated in vacuo. The residue was washed with hexane and then chromatographed on 50 g of silica gel with ethyl acetate= hexane (1:20) as solvent giving 1.2 g of solid. Crystallization from hexane containing a trace of ether gave (S)-1,1-dimethylethyl[1-(cyclohexylmethyl)-2-oxo-2-thienylethyl] carbamate as crystals; $[\alpha]_D^{26}+24°\pm1$ (c, =1.10, methanol).

A solution of 0.51 g of the above compound in 8 ml of dry tetrahydrofuran was cooled to −78° C. under argon and 3 ml of 1.0M potassium tri-sec-butylborohydride in tetrahydrofuran was added dropwise. This mixture was stirred at −78° C. for 4 hours, then quenched with 5 ml of saturated aqueous ammonium chloride, warmed to room temperature and the organic solvent removed in vacuo. The aqueous residue was diluted with 5 ml of water and 20 ml of ethyl acetate. The organic layer was separated and washed successively with two 5 ml portions of saturated aqueous ammonium chloride, 5 ml of saturated aqueous sodium bicarbonate and 5 ml of saturated aqueous sodium chloride solution, dried and the solvent removed in vacuo to give (S)-2-(tert-butoxycarbonylamino)-3-cyclohexyl-(R,S)-1-(2-thienyl)propan1-ol as a gum.

To an 18.4 g sample of the preceding gum in 330 ml of dichloromethane cooled to 0° C. was added 16.75 ml of trifluoroacetic acid. The solution was stirred overnight, cooled to 0° C. and ice cold 1N sodium hydroxide (approximately 300 ml) was added. The organic layer was separated and the aqueous layer extracted with two 350 ml portions of dichloromethane. The organic layer and extracts were combined, washed with two 250 ml portions of brine, dried ($Na_2SO_4$) and the solvent removed in vacuum to give 14.5 g of solid.

Trituration with 200 ml of hot hexane, cooling to room temperature and filtering gave 7.5 g of crystals of (4S-trans) 4-(cyclohexylmethyl)-5-(2-thienyl)-2-oxazolidinone as crystals, mp 105–108° C.

A mixture of 7.0 g of the preceding compound in 13 ml of ethanol and 132 ml of 1N sodium hydroxide was refluxed for 17 hours. The solvent was removed under vacuum and the residue extracted twice with 200 ml of dichloromethane. The combined extracts were dried ($Na_2SO_4$) and the solvent removed under vacuum to give 4.64 g of crystals, mp 62°–64° C.; $[\alpha]_D^{26}-35°\pm1$ (c, =1.145, $CH_3OH$).

REFERENCE EXAMPLE 42

(S)2-tert-Butoxycarbonylamino-4-methyl-(R,S)1-(2-furanyl)-pentan-1-ol

To 0.545 ml of furan in 10 ml of dry tetrahydrofuran under argon cooled to −20° C. was added 3.35 ml of 2.36M n-butyllithium in hexane. The solution was allowed to warm to 10° C. and stirred for 2 hours. The solution was chilled to −70C. (dry ice-acetone) and 1.70 g of N-t-butoxycarbonyl-L-leucinal in 10 ml of tetrahydrofuran was added. After 1 hour at −70° C., 10 ml of 10% ammonium chloride was added. The mixture was concentrated under vacuum, diluted with water and extracted with ether. The combined ether extracts were dried and concentrated. The residue was purified twice by thick layer chromatography on silica gel plates to give 0.20 g of product as a gum; RF 0.22 on thin layer chromatography (silica gel) with hexane-ethyl acetate (4:1) as solvent.

REFERENCE EXAMPLE 43

(S)2-tert-Butoxycarbonylamino-4-methyl-(R,S)-1-(2-thienyl)-pentan-1-ol

To a solution of 1.4 g of thiophene in 20 ml of dry tetrahydrofuran under argon was added 7.05 ml of 2.36M n-butyllithium in tetrahydrofuran. The solution was stirred at room temperature for 45 minutes and then cooled to −70° C. (dry-ice acetone bath). A solution of 1.79 g of N-tert-butoxycarbonyl-L-leucinal in 10 ml of dry tetrahydrofuran was added via syringe. The mixture was stirred (−68° C.) for one hour and quenched with 10% ammonium chloride solution. After warming to room temperature, the solvent (tetrahydrofuran) was removed under vacuum. The residual aqueous mixture was extracted with ether. The combined ether extracts were washed with 50 ml of 1N hydrochloric acid, saturated sodium bicarbonate solution, saturated sodium chloride solution and dried. The solvent was removed and the residue chromatographed on a silica gel column with hexane-ethyl acetate (gradient elution) as solvent. The product was eluted with hexane-ethyl acetate (4:1). The fractions containing product were combined and the solvent removed under vacuum to give 1.15 g of gum; RF 0.34 on TLC (silica gel) with hexane-ethyl acetate (4:1).

REFERENCE EXAMPLE 44

(S)2-Amino-4-methyl-(R)1-(2-thienyl)pentan-1-ol

A 0.81 g portion of (S)2-tert-butoxycarbonyl)amino-4-methyl-(R,S)1-(2-thienyl)pentan-1-ol was dissolved in 5 ml of dichloromethane and 2.1 ml of trifluoroacetic acid added. This mixture was stirred for 3 hours and then poured, with stirring, into 15 ml of ice-cold 2N sodium hydroxide. This mixture was diluted with 25 ml of dichloromethane, the organic layer separated and the aqueous layer extracted with 20 ml of dichloromethane. The organic layer and extract were combined, washed with saturated sodium chloride solution, dried and the solvent removed in vacuo. The residue was chromatographed on a silica gel column, eluting with ethyl acetate:hexane (1:4), giving 0.72 g of white solid; $[\alpha]_D^{26}=-141°\pm2$ (c, 0.570, methanol) which was identified (NMR spectrum) as (4S-trans)-4-(2-methylpropyl)-5-(2-thienyl)-2-oxazolidinone.

A 0.23 g portion of the above oxazolidinone was dissolved in 5 ml of ethanol and 5 ml of 1N sodium hydroxide added. This solution was refluxed for 16 hours and then concentrated in vacuo. The residue was extracted with two 10 ml of portions of dichloromethane. The extracts were combined, dried and the solvent removed in vacuo, giving 0.2 g of the desired compound; Rf 0.045 [silica gel plate-ethyl acetate:hexane (1:2)].

REFERENCE EXAMPLE 45

2-Amino1-cyclohexyl-1,2,4,5,6,7-hexadeoxy-4,7-epithio-L-arabino-Heptitol, S-oxide To a solution of 0.24 g of 2-amino-1-cyclohexyl-1,2,4,5, 6,7-hexadeoxy-4,7-epithio-L-arabino-Heptitol in 2 ml of dichloromethane is added 0.26 g of 3-chloroperbenzoic acid. After 10 minutes the solution is washed three times with 2 ml of 2M potassium carbonate. The aqueous layer is extracted with 1 ml of dichloromethane and the organic layer and extract combined and dried (Na$_2$SO$_4$). The solvent is removed and the residue chromatographed on two 20×20× 0.2 cm thick layer silica gel plate with dichloromethane methanol conc. ammonium hydroxide (9:1.2:0.2) as solvent. The band containing product is separated, washed with methanol containing 5% ammonium hydroxide to give 0.084 g of solid.

REFERENCE EXAMPLE 46

(R,S)-N-[1,4-dioxo-4-(2-benzofuranyl)-2-(phenylmethyl)butyl]-L-histidine

To a solution of 3.0 g of gamma-oxo-alpha-(2-phenylmethyl)-2-benzofuranbutanoic acid and 3.21 ml of 4-methylmorpholine in 24 ml of tetrahydrofuran, cooled to −10° C., is added 2.36 g of isobutyl chloroformate. After stirring 1 minute, 2.36 g L-histidine methyl ester dihydrochloride. The mixture is stirred at room temperature overnight and the solvent removed. To the residue is added 60 ml of ethyl acetate and the mixture washed with water (2×30 ml) 1N sodium bicarbonate (2×30 ml) and brine (20 ml). The organic layer is dried (Na$_2$SO$_4$) and the solvent removed to give 4.0 g of methyl (R,S)-N-[1,4-dioxo-4-(2-benzofuranyl)-2-(phenylmethyl)butyl]-L-histidinate as a glass. To a solution of 1.2 g of the preceding compound in 3.72 ml of methanol is added 3.72 ml of 1N sodium hydroxide. The mixture is stirred at room temperature overnight and the methanol solvent removed under vacuum. The aqueous residue is acidified with 2N citric acid (pH 5) (solid separates) and filtered to give 0.43 g of white solid. The filtrate is extracted with dichloromethane (2×15 ml), the extract dried (Na$_2$SO$_4$) and the solvent removed to give 0.50 g of light tan solid. The two crops of solid are combined to give 0.93 g of (R,S)-N-[1,4-dioxo-4-(2-benzofuranyl)-2-(phenylmethyl)butyl] -L-histidine.

REFERENCE EXAMPLE 47

(S)2-Amino-3-phenyl-(R)1-(2-furanyl)propan-1-ol

A 3.0 g sample of (4S-trans)-5-(2-furanyl)-4-(phenylmethyl)-2-oxazolidinone is dissolved in a mixture of 60 ml of ethanol and 60 ml of 1N sodium hydroxide. The solution is refluxed overnight and concentrated. The aqueous residue is extracted with 100 ml (3×) of dichloromethane, the extract dried (Na$_2$SO$_4$) and the solvent removed to give a solid. Washing with iso-octane gives 2.44 g of solid, mp. 86°–88° C.; $[\alpha]_D^{26}$−5°±1 (c,: =1.087, CH$_3$OH).

EXAMPLE 1

[S-(R*,S*,)]-4,7-Anhydro-1-cyclohexyl-2,5,6-tetradeoxy-2-[[2-[[1,4-dioxo-4-phenyl-2-(phenylmethyl)butyl]amino]-4-methyl-1-oxopentyl]amino]-L-arabino-Heptitol and
[S-(R*,R*,)]-4,7-Anhydro-1-cyclohexyl-1,2,5,6-tetradeoxy-2-[[2-[[1,4-dioxo-4-phenyl-2-(phenylmethyl)butyl]amino]-4-methyl-1-oxopentyl]-amino]-L-arabino-Heptitol To a solution of 0.268 g of gamma-oxo-alpha(phenylmethyl)benzenebutanoic acid in 2 ml of tetrahydrofuran is added 0.162 g of N,N-carbonyldiimidazole and the mixture stirred under argon for one hour. To the solution is added 0.210 g of (S)2-[(2-amino-4-methyl-1-oxopentyl)amino]-4,7-anhydro-1 -cyclohexyl-1,2,5,6-tetradeoxy-L-arabino-Heptitol prepared as in Reference Example 4 in i ml of dichloromethane. The mixture is stirred overnight, refluxed for one hour, and the solvent removed under vacuum. The residue is dissolved in 5 ml of ethyl acetate and washed three times with 1 ml portions of 1N hydrochloric acid and 1 ml portions of 1M sodium bicarbonate. The organic layer is dried (MgSO$_4$) and the solvent removed to give a solid. The preceding solid is chromatographed on silica gel with ethyl acetate-hexane (1:1) as solvent. Fractions containing the first component eluted (less polar) are combined and the solvent removed to give 0.76 g of a glass: $[\alpha]_D^{26}$−43°±1 (c, 1.00, CH$_3$OH) assigned the [S-(R*,S*)]diastereomer.

Fractions containing the more polar component are combined and the solvent removed to give a colorless solid, m.p. 118°–124° C.; $[\alpha]_D^{26}$−62°±1(c, 0.970, CH$_3$OH) assigned the [S-(R*,R*)]diastereomer.

EXAMPLE 2

4,7-Anhydro-1-cyclohexyl-1,2,5,6-tetradeoxy-2-[[2-[1,4-dioxo-4-phenyl-(R)-2-(phenylmethyl)butyl]-amino]-4-methyl-1-oxopentyl]amino]-L-arabino-Heptitol To a mixture of 0.569 g of (R)-N-[1,4-dioxo-4-phenyl-2-(phenylmethyl)butyl]-L-leucine, 0.17 ml of N-methylmorpholine in 12 ml of tetrahydrofuran cooled to −10° C. is added isobutyl chloroformate (0.20 ml). After one minute, 0.058 g of 2-amino-4,7-anhydro-1-cyclohexyl-1,2,5,6-tetradeoxy-L-arabino-Heptitol is added. The mixture is stirred overnight, filtered and the filtrate concentrated. The residue (0.84 g) is dissolved in 25 ml of ethyl acetate and the solution washed three times with 5 ml portions each of 1N hydrochloric acid, 1M sodium bicarbonate. The organic layer is dried (Na$_2$SO$_4$) and the solvent removed and crystallized from hexane-diisopropyl ether to give 0.61 g of crystals: $[\alpha]_D^{26}$−43°±1 (c, 1.0, OH$_3$OH), m.p. 140°–142° C.

EXAMPLE 3

[N(1S)-[N[1R,(1R*,2S*)]alpha S*]]N-[1-[[[1-(cyclohexylmethyl)-2-(2-furanyl)-2-hydroxyethyl]amino]carbonyl]-3-methylbutyl]-gamma-oxo-alpha-(phenylmethyl)benzenebutanamide To a mixture of 0.78 g of gamma-oxo-alpha(phenylmethyl)benzenebutanoic acid, 0.40 ml of triethylamine in 10 ml of dichloromethane, under argon, is added 0.46 ml of diethoxyphosphoryl cyanide. After one minute, 0.80 g of N-(L-leucyl)-2-amino-3-cyclohexyl-(R)-1-(2-furanyl)propan-1-ol in 5 ml of dichloromethane is added and the mixture stirred overnight and then refluxed for 2 hours. The solvent is removed and the residue chromatographed on silica gel by HPLC with a Water-Prep. 500A instrument and hexane-ethyl acetate (2:1) as eluent. Fractions containing the first component eluted are combined and the solvent removed to give 0.44 g of the product of the Example as a glass: $[\alpha]_D^{26}$−37°≅1 (c, 1.126, CH$_3$OH). Fractions containing the slower moving component are combined and solvent removed to give 0.39 g of a glass: Crystallization from methanol gives crystals, m.p. 110°–120° C.: $[\alpha]_D^{-62°\pm1}$ (c, 1.00CH$_3$OH): [N(1S)-[N[1R*(1R*,2S*)]alpha R*]]diastereomer of the product of the Example.

EXAMPLE 4

[S-R*,S*)]-4,7-anhydro-1-cyclohexyl-1,2,5,6-tetradeoxy-2-[[2-[[1,4-dioxo-2-(phenylmethyl)-4-[3-(trifluoromethyl)phenyl]butyl]amino]-4-methyl-1-oxopentyl]amino]-L-arabino-Heptitol To a solution of 0.200 g of (R)-N-[1,4-dioxo-2-(phenylmethyl)-4-[3-trifluoromethyl)phenyl]butyl]-L-leucine and 49 µl of N-methylmorpholine in 4 ml of tetrahydrofuran (chilled to −10° C.) is added 58 µl of isobutyl chloroformate. After one minute, 0.096 g of (S)-2-[[(2-amino-4-methyl-1-oxopentyl)amino]-4,7-anhydro-1-cyclohexyl-1,2,5,6 -tetradeoxy-L-arabino-Heptitol is added. The cooling bath is removed and the mixture stirred overnight at room temperature. The solvent is removed and the residue dissolved in 10 ml of ethyl acetate. The solution is washed with 2 ml portions of 1N hydrochloric acid, 1M sodium bicarbonate, and dried (Na$_2$SO$_4$). The solvent is removed to give 0.230 g of a light yellow glass: $[\alpha]_D^{26}$ −34°±1 (c, 1.021, CH$_3$OH).

EXAMPLE 5

[S-(R*,S*)]-1,4-Anhydro-1-cyclohexyl-1,2,5,6-tetradeoxy-2-[[2-[[1,4-dioxo-4-phenyl-2-(phenylmethyl)butyl]amino]-3-(1H-imidazol-4-yl)-1-oxo-propyl]amino]-L-arabino-Heptitol To a solution of 0,064 g of (R)-γ-oxo-α-(phenylmethyl)benzenebutanoic acid, 25 µl of N-methylmorpholine in 0.5 ml of tetrahydrofuran cooled to −10° C. is added 30 µl of isobutyl chloroformate. After one minute, 0.070 g of 2-[[2-amino-3-(1H-imidazol-4-yl)-1-oxopropyl]amino]-4,7-anhydro-1-cyclohexyl-1,2,5,6-tetradeoxy-L-arabino-Heptitol in 0.5 ml of tetrahydrofuran is added. The mixture is stirred overnight and refluxed for 0.5 hour. The solvent is removed and the residue dissolved in 5 ml of ethyl acetate. The solution is washed three times with 1 ml each of 2N sodium carbonate, 1M citric acid-1M sodium citrate buffer and brine. The organic layer is dried (Na$_2$SO$_4$) and the solvent removed. The residue is chromatographed on two 20×20× 0.2 cm thick layer silica gel plates with dichloromethane-methanol-ammonium hydroxide (9:1.2:0.2) as solvent to give 0.054 g of a glass, m.p. 95°–115° C.: $[\alpha]_D^{26}$ −30°±1 (c, 0.942, CH$_3$OH).

EXAMPLE 6

[S-(R*,S*)]-4,7-Anhydro-1-cyclohexyl-1,2,5,6-tetradeoxy-2-[[2-[[2-[[1,4-dioxo-4-(2-furanyl)-2-(phenylmethyl)butyl]amino]-4-methyl-1-oxopentyl]amino]-L-arabino-Heptitol To a solution of 0.160 g of 7-oxo-α-(phenylmethyl)-2-furanbutanoic acid and 68 µl of 4-methylmorpholine in 5 ml tetrahydrofuran chilled to −10° C. is added 80.4 µl of isobutyl chloroformate. After one minute, 0.200 g of (S)-2-[(2-amino-4-methyl-1-oxopentyl)amino]-4,7-anhydro-1-cyclohexyl-1,2,5,6-tetradeoxy-L-arabino-Heptitol is added. The mixture is stirred overnight (cooling bath removed) and the solvent removed. The residue is dissolved in 12 ml of ethyl acetate and the solution washed with 4 ml each of water, 1N hydrochloric acid, 1M sodium bicarbonate, and dried (Na$_2$SO$_4$). The solvent is removed to give 0.25 g of a gum. This gum is chromatographed on four 20×20×0.2 cm thick layer plates with ethyl acetate-hexane (2:1) as solvent. The faster moving component is removed (with CH$_3$OH) and the solvent removed to give 0.095 g of the product of the Example as a white solid; $[\alpha]_D^{26}$ −45°±2 (c, 0.457, CH$_3$OH). The slower moving component is removed from the plates (with CH3OH) and the solvent removed to give 0.100 g of [S-(R*,R*)]-diastereomer of the product of the Example as a white solid; $[\alpha]_D^{26}$ −72°±3 (c, 0.329, CH$_3$OH).

EXAMPLE 7

S-(R*,S*)]-4,7-anhydro-1-cyclohexyl-1,2,5,6-tetradeoxy-2-[[3(1H-imidazol-4-yl)-2-[[-(1-naphthalenylmethyl)-1,4-dioxo-4-(2-thiazolyl)butyl]amino]-1-oxopropyl]amino]-L-arabino (and D-xylo)-Heptitol To a solution of 0.232 g of (R)-alpha-1-naphthalenylmethyl-gamma-oxo-2-thiazolebutanoic acid and 70 µL of N-methylmorpholine in 4 ml of tetrahydrofuran chilled to −10° C. is added 93 µL of isobutyl chloroformate. After 1 minute 0.25 g of 2-[[2-amino-3-(1H-imidazol-4-yl)-1-oxopropyl]amino]-4,7 -anhydro-1-cyclohexyl-1,2,5,6-tetradeoxy-L-arabino (and D-xylo)-Heptitol (1:1 mixture of diastereomers) in 4 ml of tetrahydrofuran is added and the mixture stirred for overnight. The solvent is removed under vacuum and the residue dissolved in 10 ml of ethyl acetate. The solution is washed with three 1-ml portions of 2M sodium carbonate, 1M-citric acid-1M-sodium citrate buffer(methanol added to dissolve solid) and brine. The organic layer is dried (Na$_2$SO$_4$) and the solvent removed to give 0.42 g of solid. This solid is chromatographed on four 20×0.2 cm thick layer silica gel plates. The product fractions are washed from the plate with ammonium hydroxide in methanol and the combined washings concentraed under vacuum and dried to give 0.13 g of a glass: $[\alpha]_D^{26}$ +3°±1 (c, 0.924, CH$_3$OH).

EXAMPLE 8

[S-(R*,S*)]-4,7-Anhydro-1-cyclohexyl-1,2,5,6-tetradeoxy-2-[[4-methyl-2-[[2-(1-naphthalenylmethyl)-1,4-dioxo-4-(2-thiazolyl)butyl]amino]-1-oxopentyl]amino]-L-arabino-Heptitol To a mixture of 0,134 g of (R)-alpha-1-naphthalenylmethyl-gamma-oxo-2-thiazolebutanoic acid and 47 µl of N-methylmorpholine in 2 ml of tetrahydrofuran chilled to −10° C. is added 56 µl of isobutyl chloroformate. After 1 minute is added 0.136 g of (S)-2-[(2-amino-4-methyl-1-oxopentyl)amino]-4,7-anhydro-1-cyclohexyl-1,2,5,6-tetradeoxy-L-arabino-Heptitol in 1 ml of tetrahydrofuran and the mixture stirred for 3 hours. The solvent is removed, the residue dissolved in 10 ml 20 of ethyl acetate and the solution washed with 1N HCl, 1M sodium bicarbonate, brine and dried (Na$_2$SO$_4$). The solvent is removed to give 0.13 g of a glass: $[\alpha]_D^{26}$ +5°±1 (c, 1.00, CH$_3$OH).

EXAMPLE 9

[S-(R*,S*)]-4,7-anhydro-1-cyclohexyl-1,2,5,6-tetradeoxy-2-[[4-methyl-2-[[2-(1-naphthalenylmethyl)-1,4-dioxo-4-(2-thiazolyl)butyl]amino]-1-oxopentyl]amino]-D-xylo-Heptitol To a mixture 0,134 g of (R)-alpha-1-naphthalenylmethyl-gamma-oxo-2-thiazolebutanoic acid and 47 µl of N-methylmorpholine in 2 ml of tetrahydrofuran chilled to −10° C. is added 56 µl of isobutylchloroformate. After 1 minute is added 0.136 g of (S)-2-[(2-amino-4-methyl-1-oxopentyl)amino]-4,7-anhydro-1-cyclohexyl-1,2,5,6-tetradeoxy-D- xylo-Heptitol in 1 ml of tetrahydrofuran. The mixture is stirred 3 hours and the solvent removed. The residue is dissolved in 5 ml of ethyl acetate and washed with 1M sodium bicarbonate, 1N hydrochloric acid, brine and dried (MgSO$_4$). The solvent is removed and the residue chromatographed on four 20×20×2 cm thick layer silica gel plates with dichloromethane-methanol-ammonium hydroxide (95:0.75:0.1) as solvent. The bands are washed from plate with 16% ammonium hydroxide in methanol and the solvent removed. The residue is dissolved in dichloromethane and filtrate is concentrated to give 0.12 g of a glass: $[\alpha]_D^{26}$+11°±1 (c, 1.023, CH$_3$OH).

EXAMPLE 10

[S-(R*,S*)]-1-Cyclohexyl-1,2,4,5,6,7-hexadeoxy-2-[[2-[[1,4-dioxo-4-phenyl-2-(phenylmethyl)butyl]-amino]-4-methyl-1-oxopentyl]amino]-4,7-epithio-L-arabino-Heptitol To a solution of (R)-gamma-oxo-α-(phenylmethyl)benzenebutanoic acid (69 mg) and 20 µl of H-methylmorpholine in 0.5 ml of tetrahydrofuran cooled to −10° C. is added 24 µl of isobutyl chloroformate. After 1 minute is added 39 mg of 2-amino-1-cyclohexyl-1,2,4,5,6,7-hexadeoxy-4,7-epithio-L-arabino-Heptitol and the mixture stirred overnight. The mixture is diluted with 5 ml of dichloromethane, washed with water, sodium bicarbonate, and potassium hydrogen sulfate solution (0.35M). The organic layer is dried (MgSO$_4$) and the solvent removed. The residue (oil) is chromatographed on two 20×20×0.2 cm thick layer silica gel plates with hexane-ethyl acetate (1:1) as solvent. The product band is removed and washed from the silica gel with 10% methanol in ethyl acetate. The solvent is removed to give 57 mg of the product as a solid; $[\alpha]_D^{26}$ −12°±1 (c, 0.731, CH$_3$OH).

EXAMPLE 11

[S-(R*,S*)]-4,7-Anhydro-1-cyclohexyl-2-[[2-[[2-(cyclohexylmethyl)-4-(2-furanyl)-1,4-dioxobutyl]amino]-4-methyl-1-oxopentyl]amino]-1,2,5,6-tetradeoxy-L-arabino-Heptitol and [8-(R*,R*)]diastereomer, To a stirred solution of 0.164 g of alpha(cyclohexylmethyl)gamma-oxo-2-furanbutanoic acid and 68 µl of 4-methylmorpholine in 5 ml of tetrahydrofuran cooled to −10° C. is added 80.4 µl of isobutyl chloroformate. After 1 minute, 0.200 g of (S)-2-[(2-amino-4-methyl-1-oxopentyl)amino]-4,7-anhydro-1-cyclohexyl-1,2,5,6-tetradeoxy-L-arabino-Heptitol is added and the mixture stirred at room temperature overnight. The solvent is removed, the residue dissolved in ethyl acetate (12 ml) and the solution washed with 4 ml each of water, 1N hydrochloric acid, 1M sodium bicarbonate and brine. The organic layer is dried (Na$_2$SO$_4$) and the solvent removed under vacuum. The residue is chromatographed on thick layer silica gel plates with ethyl acetate-hexane (2.5:1) as solvent to give 0.168 g of the [S-(R*,S)*]diastereomer as a white foam: $[\alpha]_D^{26}$ −40°±1 (c, 1.20, CH$_3$OH) and 0.110 g of the [S-(R*,R*)]diastereomer as a white foam: $[\alpha]_D^{26}$−56°±1 (c, 0.888, C$_3$OH).

EXAMPLE 12

[N(1S)-[N[1R*,(1R*,2S*)], alpha S*]]-N-[1-[[[1-(cyclohexylmethyl)-2-hydroxy-2-(2-thienyl)ethyl]amino]carbonyl]-3-methylbutyl]-gamma-oxo-alpha(phenylmethyl)-benzenebutanamide To a stirred solution of 0.250 g of (R)-N-[1,4-dioxo-4-phenyl-2-(phenylmethyl)butyl]-L-leucine and 72 µl of 4-methylmorpholine in 6 ml of tetrahydrofuran, cooled to −10° C. is added 84 µl of isobutyl chloroformate. After 1 minute is added 0.148 g of (S)2-amino-3-cyclohexyl-(R)-1-(2-thienyl)propan-1-ol and the mixture stirred at room temperature 20 hours. The solvent is removed under vacuum and the residue dissolved in 15 ml of ethyl acetate. The solution is washed with 5 ml each of water, 1N hydrochloric acid, 1M sodium bicarbonate, brine and dried (Na$_2$SO$_4$). The solvent is removed to give 0.357 g of product as a white foam: $[\alpha]_D^{26}$−42°±1(c, 1.04, CH$_3$OH).

EXAMPLE 13

[S-(R*,R*) and S-(R*,S*)]4,7-Anhydro-2-[[2-[[4-(2-benzofuranyl)-1,4-dioxo-2-(phenylmethyl)butyl]amino]-3-(1H-imidazol-4-yl)-1-oxopropyl]amino]-1-cyclohexyl-1,2,5,6-tetradeoxy-L-arabino-Heptitol To a solution of 0,133 g of gamma-oxo-alpha( 2-phenylmethyl)-2-benzofuranbutanoic acid and 47.49 µl of 4-methylmorpholine in 3 ml of tetrahydrofuran cooled to −10° C. is added 56.03 µl of isobutyl chloroformate. The mixture is stirred 1 minute and 0.150 g of 2-[[2-amino-3-(1H-imidazol-4-yl)1 -oxopropylamino]-4,7-anhydro-1-cyclohexyl-1,2,5,6-tetradeoxy-L-arabino-Heptitol is added. The mixture is stirred at room temperature overnight and the solvent removed under vacuum. Ethyl acetate is added to the residue and the mixture washed with water, 1M sodium bicarbonate, brine and dried (Na$_2$SO$_4$). The solvent is removed and the residue purified by chromatography on silica gel with dichloromethane-methanol-ammonium hydroxide (9.5:0.75:0.1) as solvent to give the product as a white glass.

EXAMPLE 14

[S-(R*,S*)]-1-cyclohexyl-1,2,4,5,6,7-hexadeoxy-2-[[2-[[1,4-dioxo-4-phenyl-2-(phenylmethyl)-butyl]amino]-4-methyl-1-oxopentyl] amino]-4,7-epithio-L-arabino-Heptitol, S-oxide To a solution of 0.136 g of (R)-N-[1,4-dioxo-4-phenyl-2-(phenylmethyl)butyl]-L-leucine and 40 µl of 4-methylmorpholine in 1 ml of tetrahydrofuran (cooled to −10° C.) is added 48 µl of isobutyl chloroformate. The mixture is stirred i minute and 84 mg of 2-amino-1-cyclohexyl-1,2,4,6,7-hexadeoxy-4,7 -epithio-L-arabino-Heptitol, S-oxide in 0.5 ml of tetrahydrofuran is added. The mixture is stirred at room temperature overnight and the solvent removed. The residue in 5 ml of ethyl acetate is washed with water (2 ml) and twice with 2 ml each of. 2N sodium carbonate and 0.5 N-citric acid-socium citrate buffer. The organic layer is dried (Na$_2$SO$_4$) and the solvent removed to give 0.13 g of solid. Chromatography on thick layer silica gel plates with dichloromethane-methanol-ammonium hydroxide (9.5:0.75:0.1) as solvent gives 90 mg of product as a glass.

EXAMPLE 15

[S-(R*,R*,)] and [S-(R*,S*)]-4,7-Anhydro-1-cyclohexyl-1,2,5,6-tetradeoxy-2-[[4-methyl-2-[[4-[3-[(methylamino)sulfonyl]phenyl]-1,4-dioxo-2-(phenylmethyl)butyl]amino]-1-oxopentyl]amino]-L-arabino-Heptitol As described for Example 6, 0.279 g of 3-(methylaminosulfonyl)gamma-oxo-α-(phenylmethyl) benzenebutanoic acid, mp 130°–133° C. is coupled with 0.250 g of (S)-2-[[(2-amino-4-methyl-1-oxopentyl)amino]-4,7-anhydro-1-cyclohexyl-1,2,5,6-tetradeoxy-L-arabino-Heptitol in 8 ml of tetrahydrofuran. The product 0.470 g is chromatographed on four 20×20×0.2 cm thick layer plates with ethyl acetate-hexane (5:1) as solvent to give the [S-(R*,S*)] diastereomer (0.157 g) as a white foam; $[\alpha]_D^{26}$ –45°±1(c, 1.034, $CH_3OH$) and the [S-(R*,R*)] diastereomer as a white foam; $[\alpha]_D^{26}$ –51°±1(c, 1.057, $CH_3OH$).

EXAMPLE 16

[S-(R*,S*)]-4,7-Anhydro-1-cyclohexyl-1,2,5,6-tetradeoxy-2-[[-[[1,4-dioxo-2-(phenylmethyl-4-(2-thienyl)butyl]amino]-4-methyl-1-oxo-pentyl]amino]-L-arabino-Heptitol As described for Example 2, a mixture of 0.266 g of (R)-N-[1,4-dioxo-2-(phenylmethyl)-4-(2-thienyl)butyl]-L-leucine; $[\alpha]_D^{26}$–21°±1(c, 1.028, $CH_3OH$) in 4 ml of tetrahydrofuran is added 75.5 µl of 4-methylmorpholine. After five minutes the solution is cooled to –10° C. and 89.1 µl of isobutyl chloroformate added. After 1 minute 0.148 g of 2-amino-4,7-anhydro-1-cyclohexyl-1,2,5,6-tetradeoxy-L-arabino-Heptitol. The product (0.376 g) is isolated and dried to give a foam; $[\alpha]_D^{26}$–524°±1(c, 1.023, $CH_3OH$).

EXAMPLE 17

[S-(R*,S*)]-1-Cyclohexyl-1,2,4,5,6,7-hexadeoxy-2-[[2-[[1,4-dioxo-2-(phenylmethyl)-4-(2-thienyl)butyl]amino]-4-methyl-1-oxopentyl]amino]-4,7-epithio-L-arabino-Heptitol To a mixture of 0.219 g of (R)-N-[1,4-dioxo-2-(phenylmethyl)-4-(2-thienyl)butyl]-L-leucine in 4 ml of tetrahydrofuran is added 61 µl of 4-methylmorpholine. The solution is cooled to –10° C. and 72 µl of isobutyl chloroformate added. After 1 minute 0.122 g of 2-amino-1-cyclohexyl-1,2,4,5,6,7-hexadeoxy-4,7-epithio-L-arabino-Heptitol is added and the mixture stirred overnight. The solvent is removed and the residue dissolved in 5 ml of ethyl acetate. The solution is washed with 1 ml of 1N HCl (3×) and with 1 ml of sodium bicarbonate (3×) and dried over $Na_2SO_4$. The solvent is removed and the residue (0.27 g) crystallized from hexane-diisopropyl ether and recrystallized from diisopropyl ether to give 0.166 g of crystals, mp 162°–163° C.: $[\alpha]_D^{26}$28°±1(c, 0.998, $CH_3OH$).

EXAMPLE 18

[S-(R*,R*) and S-(R*,S*)]-4,7-Anhydro-1-cyclohexyl-1,2,5,6-tetradeoxy-2-[[2-[[1,4-dioxo-2-(phenylmethyl)-4-(2-thienyl)butyl]amino]-3-(1H-imidazol-4-yl-1-oxo-propyl]amino]-L-arabino-Heptitol To a solution of 0.105 g of gamma-oxo-α-(phenylmethyl)-2-thiophenebutanoic acid in 1 ml of tetrahydrofuran is added 44 µl of 4-methylmorpholine and the mixture chilled to –10° C. To the solution is added 52 µl of isobutyl chloroformate. After 1 minute is added 0.14 g of 2-[[2-amino-3-(1H-imidazol-4-yl)-1-oxopropyl]amino]-4,7-anhydro-1-cyclohexyl-1,2,5,6-tetradeoxy-L-arabino-Heptitol in 2 ml of chloroform. The mixture is stirred overnight at room temperature and refluxed for 2 hours. The solvent is removed, the residue dissolved in 10 ml of ethyl acetate and the solution washed 3 times with 3 ml of titrate buffer [2N citric acid-1N NaOH (1:1)] and three times with 3 ml of 1M sodium bicarbonate and dried ($Na_2SO_4$). The solvent is removed and the residue chromatographed on four 20×20×0.2 thick layer silica gel plates with dichloromethane-methanol-ammonium hydroxide (9:1 2:0.2) as solvent. The band containing product is collected and eluted with methanol-ammonium hydroxide (9:1). The eluate is filtered through diatomaceous earth and the filtrate concentrated to give 0.14 g of a glass: $[\alpha]_D^{26}$–32° ±1(c, 0.912, $CH_3OH$).

We claim:

1. A compound of the formula:

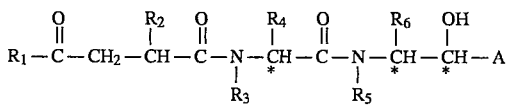

wherein $R_1$ is: phenyl,

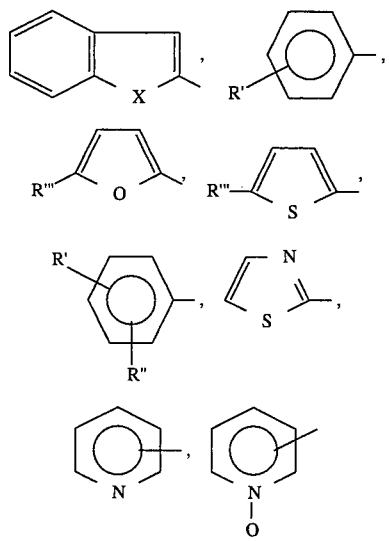

R' is hydrogen, chloro, fluoro, methoxy, methyl, trifluoromethyl, $SO_2NH_2$,

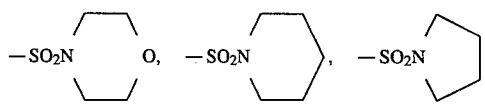

—$SO_2NH$loweralkyl($C_1$–$C_6$); —$SO_2N$(lower alkyl)$_2$;
R'' is chloro, fluoro, methyl, methoxy;
R''' is hydrogen, chloro, fluoro, loweralkyl($C_1$–$C_6$);

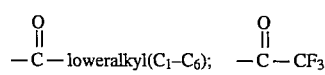

$R_2$ is phenylmethyl, cyclohexylmethyl, lower alkyl ($C_1$–$C_6$),

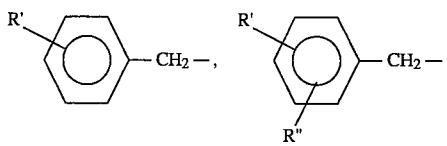

(wherein R' and R'' are as defined above), 1-naphthalenylmethyl, (benzo[b]-thien-3-yl)methyl, (benzo[b]- thien-2-yl)methyl, (3-benzofuranyl)methyl, (2-benzofuranyl)methyl;

$R_3$ is hydrogen or methyl; $R_4$ is alkyl($C_1$–$C_8$), phenylmethyl, cyclohexylmethyl, 4-imidazolylmethyl, (4-imidazolyl)$CH_2$X, X-alkyl ($C_1$–$C_8$), —($C_2$)$_n$N[loweralkyl($C_1$–$C_3$)]$_2$, —($CH_2$)$_n$—NH alkyl ($C_1$–$C_3$), X-cyclohexyl, —($CH_2$)$_n$—X-alkyl ($C_1$–$C_3$), —X—$CH_2CH_2$N[alkyl($C_1$–$C_3$)]$_2$ (where X is —O— or —S— and n is an integer from 1 to 4) and moieties of the formula:

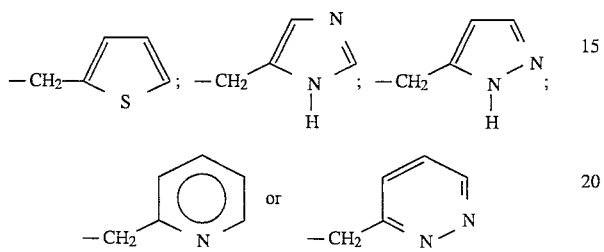

$R_5$ is hydrogen or methyl; $R_6$ is alkyl($C_1$–$C_6$), phenylmethyl, cyclohexylmethyl, or

and A is

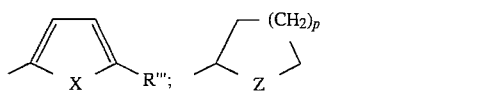

where Z is O, S, SO, $SO_2$, P is 1 or 2 and X is —O— or —S— (where R''' is as defined above).

2. A compound of the formula:

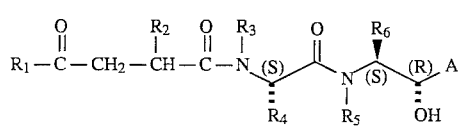

wherein $R_1$ is: phenyl,

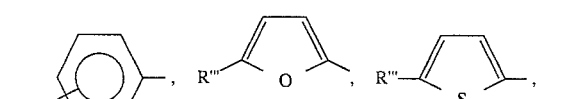

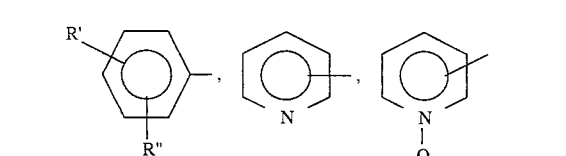

R' is hydrogen, chloro, fluoro, methoxy, methyl, trifluoromethyl, $SO_2NH_2$,

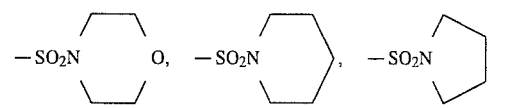

—$SO_2$NHloweralkyl($C_1$–$C_6$); —$SO_2$N(lower alkyl ($C_1$–$C_6$))$_2$;

R' is chloro, fluoro, methyl, methoxy;

R''' is hydrogen, chloro, fluoro, loweralkyl($C_1$–$C_6$);

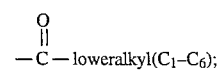

$R_2$ is phenylmethyl, cyclohexylmethyl, lower alkyl ($C_1$–$C_6$),

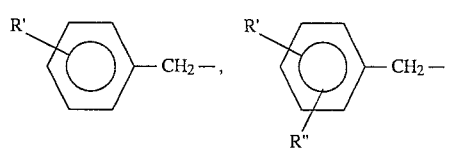

(wherein R' and R'' are as defined above), or 1-naphthalenylmethyl;

$R_3$ is hydrogen or methyl; $R_4$ is alkyl($C_1$–$C_8$), or 4-imidazolylmethyl;

$R_5$ is hydrogen; $R_6$ is alkyl($C_1$–$C_6$), phenylmethyl, or cyclohexylmethyl, and A is

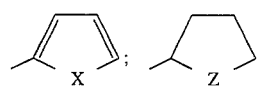

where Z is O, S, SO and X is —O— or —S—.

3. A compound according to claim 1 wherein the α-amino acids have the natural L configuration.

4. A compound according to claim 2 wherein the C-terminal unit is of the formula:

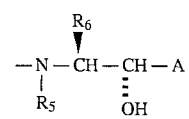

wherein $R_1$ is phenyl, 3-(trifluoromethyl)phenyl, 4-chlorophenyl, 3-chlorophenyl, 3-fluorophenyl, 3-(aminosulfonyl)phenyl, 3-(4-morpholinylsulfonyl)phenyl, 2furanyl, 2-thienyl, 5-chloro-2-furanyl, 5-chloro-2-thienyl, 4-chloro-3-(aminosulfonyl)phenyl, 5-methyl-2-furanyl; $R_2$ is phenylmethyl, (4-methoxyphenyl)methyl, 1-naphthalenylmethyl, (4-chlorophenyl)methyl, (3-fluorophenyl)methyl; $R_3$ is hydrogen; $R_4$ is alkyl($C_1$–$C_6$),

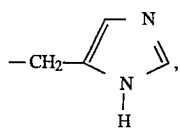

$R_5$ is hydrogen; $R_6$ is alkyl($C_1$–$C_6$) or cyclohexylmethyl.

5. A compound according to claim 2 wherein the C-terminal unit is of the formula:

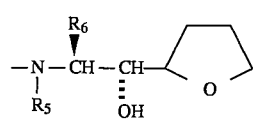

wherein $R_1$ is phenyl, 3-(trifluoromethyl)phenyl, 4-chlorophenyl, 3-chlorophenyl, 3-fluorophenyl, 3-(aminosulfonyl)phenyl, 3-(4-morpholinylsulfonyl)phenyl, 2-furanyl, 2-thienyl, 5-chloro-2-furanyl, 5-chloro-2-thienyl, 4-chloro-3-(aminosulfonyl)phenyl, 5-methyl-2-furanyl; $R_2$ is phenylmethyl, (4-methoxyphenyl)methyl, 1-naphthalenylmethyl, (4-chlorophenyl)methyl, (3-fluorophenyl)methyl; $R_3$ is hydrogen; $R_4$ is alkyl($C_1$–$C_6$),

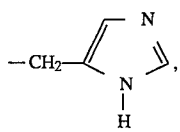

$R_5$ is hydrogen; $R_6$ is alkyl($C_1$–$C_6$) or cyclohexylmethyl.

6. A compound according to claim 2 wherein the C-terminal unit is of the formula:

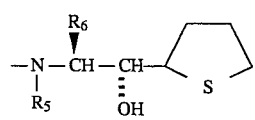

wherein $R_1$ is phenyl, 3-(trifluoromethyl)phenyl, 4-chlorophenyl, 3-chlorophenyl, 3-fluorophenyl, 3-(aminosulfonyl)phenyl, 3-(4-morpholinylsulfonyl)phenyl, 2-furanyl, 2-thienyl, 5-chloro-2-furanyl, 5-chloro-2-thienyl, 4-chloro-3-(aminosulfonyl)phenyl, 5-methyl-2-furanyl; $R_2$ is phenylmethyl, (4-methoxyphenyl)methyl, 1-naphthalenylmethyl, (4-chlorophenyl)methyl, (3-fluorophenyl)methyl; $R_3$ is hydrogen; $R_4$ is alkyl($C_1$–$C_6$),

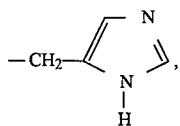

$R_5$ is hydrogen; $R_6$ is alkyl($C_1$–$C_6$) or cyclohexylmethyl.

7. A compound according to claim 5, [S-(R*,S*)]-4,7-anhydro-1-cyclohexyl-1,2,5,6-tetradeoxy-2-[[2-[[1,4-dioxo-4-phenyl-2-(phenylmethyl)butyl]amino]-4-methyl-1-oxopentyl]amino]-L-arabino-Heptitol.

8. A compound according to claim 5, S-(R*,S*)]-4,7-anhydro-1-cyclohexyl-1,2,5,6-tetradeoxy-2-[[2-[[1,4-dioxo-2-(phenylmethyl)-4-[3-(trifluoromethyl)phenyl]butyl]amino]-4-methyl-1-oxopentyl]amino] -L-arabino-Heptitol.

9. A compound according to claim 5, where $R_1$ is 2-furanyl, $R_2$ is phenylmethyl, $R_3$ and $R_5$ are hydrogen, $R_4$ is $CH_2CH(CH_3)_2$, and $R_6$ is cyclohexylmethyl.

10. A compound according to claim 5, where $R_1$ is 2-furanyl, $R_2$ is (4-methoxyphenyl)methyl, $R_3$ and $R_5$ are hydrogen, $R_4$ is

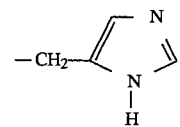

and $R_6$ is cyclohexylmethyl.

11. A compound according to claim 5, where $R_1$ is 2-furanyl, $R_2$ is 1-naphthalenylmethyl, $R_3$ and $R_5$ are hydrogen, $R_4$ is

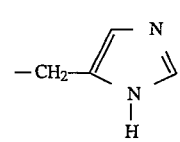

and $R_6$ is cyclohexylmethyl.

12. A compound according to claim 5, where $R_1$ is phenyl, $R_2$ is phenylmethyl, $R_3$ and $R_5$ are hydrogen, $R_4$ is

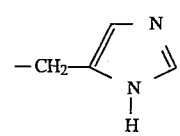

and $R_6$ is cyclohexylmethyl.

13. A compound according to claim 5, where $R_1$ is phenyl, $R_2$ is (4-methoxyphenyl)methyl, $R_3$ and $R_5$ are hydrogen, $R_4$ is

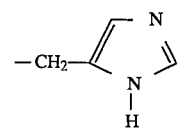

and $R_6$ is cyclohexylmethyl.

14. A compound according to claim 5, where $R_1$ is 2-thienyl, $R_2$ is (4-methoxyphenyl)methyl, $R_3$ and $R_5$ are hydrogen, $R_4$ is

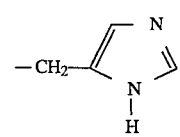

and $R_6$ is cyclohexylmethyl.

15. A compound according to claim 5, where $R_1$ is 4-chloro-3-aminosulfonylphenyl, $R_2$ is (4-methoxyphenyl)methyl, $R_3$ and $R_5$ are hydrogen, $R_4$ is

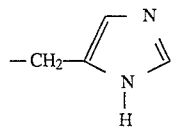

and R$_6$ is cyclohexylmethyl.

16. A compound according to claim 5, where R$_1$ is 5-chloro-2-thienyl, R$_2$ is phenylmethyl, R$_3$ and R$_5$ are hydrogen, R$_4$ is

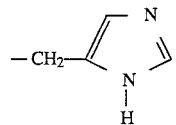

and R$_6$ is cyclohexylmethyl.

17. A compound according to claim 6, where R$_1$ is phenyl, R$_2$ is (4-methoxyphenyl)methyl, R$_3$ and R$_5$ are hydrogen, R$_4$ is

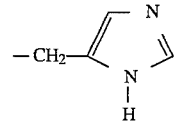

and R$_6$ is cyclohexylmethyl.

18. A compound according to claim 6, where R$_1$ is 2-furanyl, R$_2$ is phenylmethyl, R$_3$ and R$_5$ are hydrogen, R$_4$ is

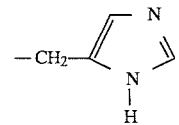

and R$_6$ is cyclohexylmethyl.

19. A compound according to claim 6, where R$_1$ is 2-thienyl, R$_2$ is (4-methoxyphenyl)methyl, R$_3$ and R$_5$ are hydrogen, R$_4$ is

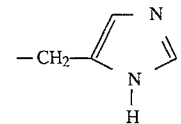

and R$_6$ is cyclohexylmethyl.

20. A compound according to claim 6, where R$_1$ is 3-(aminosulfonyl)phenyl, R$_2$ is phenylmethyl, R$_3$ and R$_5$ are hydrogen, R$_4$ is

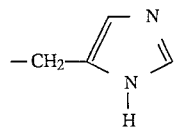

and R$_6$ is cyclohexylmethyl.

21. A method of treating renin-associated hypertension in a warm-blooded animal which comprises administering to the animal a hypotensive amount of a compound of claim 1.

22. A parenteral composition in dosage unit form comprising a compound of claim 1 and a parenterally acceptable carrier.

23. A process for preparing the compounds of claim 1 which comprises activating a compound of the formula:

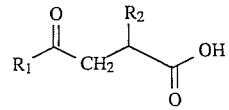

with a peptide coupling reagent having an activating moiety selected from the group of N,N'-dicyclohexylcarbodiimide, N,N'-dicyclohexylcarbodiimide plus hydroxysuccinimide, N,N'-dicyclohexylcarbodimide plus 1-hydroxy-benzotriazole, 1-benzotriazolyl diethyl phosphate, 1-chloro-N,N,2-trimethyl-1-propen-1-amine, diphenyl phosphoryl azide, diethylphosphorochloridate, di-loweralkyl (C$_1$–C$_8$) phosphorochloridates, diphenyl phosphorochloridate, phenyl phosphorodichloridate benzotriazol-1-yloxytris(dimethylamino)-phosphonium hexafluorophosphate, N,N'-bis[2-oxo-3-oxazolidinyl]-phosphorodiamidic chloride, diphenylphosphinyl chloride, diethoxyphosphoryl cyanide, bis(pentafluorophenyl)sulfite, N,N'-carbonyldiimidazole, or isobutyl chloroformate plus N-methylmorpholine, 2-chloro-1-methylpyridinium iodide, N,N'-disuccinimidyl carbonate, 1-bromo-N,N,2-trimethyl-1-propen-1-amine, 1-benzotriazolyl diethyl phosphate, to give an intermediate of the formula:

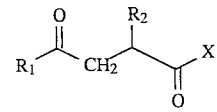

(where X is an activating moiety, halogen, or pentafluorophenyloxy); reacting the intermediate at −10° C. to 25° C. in tetrahydrofuran, dioxane, dichloromethane or ethyl acetate with a 1-amino-2-hydroxy compound of formula:

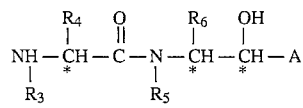

to give the compounds of claim 1.

24. A process for preparing the compounds of claim 1 which comprises activating a compound of the formula:

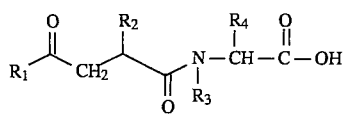

with a peptide coupling reagent having an activating moiety selected from the group of N,N'-dicyclohexylcarbodiimide, N,N'-dicyclohexylcarbodiimide plus hydroxysuccinimide, N,N'-dicyclohexylcarbodiimide plus 1-hydroxy-benzotriazole, 1-benzotriazolyl diethyl phosphate, 1-chloro-N,N,2-trimethyl-1-propen-1-amine, diphenyl phosphoryl azide, diethylphosphorochloridate, di-loweralkyl ($C_1$–$C_8$) phosphorochloridates, diphenyl phosphorochloridate, phenyl phosphorodichloridate benzotriazol-1-yloxytris(dimethylamino)phosphonium hexafluorophosphate, N,N'-bis[2-oxo-3-oxazolidinyl]-phosphorodiamidic chloride, diphenylphosphinyl chloride, diethoxyphosphoryl cyanide, bis(pentafluorophenyl)sulfite, N,N'-carbonyldiimidazole, or isobutyl chloroformate plus N-methylmorpholine, 2-chloro-1-methylpyridinium iodide, N,N'-disuccinimidyl carbonate, 1-bromo-N,N,2-trimethyl-1-propen-1-amine, 1-benzotriazolyl diethyl phosphate, to give an intermediate of the formula:

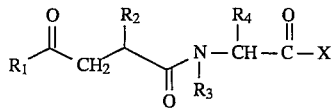

(where X is an activating moiety, halogen, pentafluorophenyloxy); reacting the intermediate at −10° C. to 25° C. in a solvent such as tetrahydrofuran, dioxane, dichloromethane or ethyl acetate with a compound of the formula:

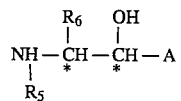

to give the compounds of claim 1.

* * * * *